United States Patent
Nussbaumer et al.

(10) Patent No.: US 12,152,064 B2
(45) Date of Patent: Nov. 26, 2024

(54) BTNL3/8 TARGETING CONSTRUCTS FOR DELIVERY OF PAYLOADS

(71) Applicants: KING'S COLLEGE LONDON, London (GB); GAMMADELTA THERAPEUTICS LIMITED, London (GB)

(72) Inventors: Oliver Nussbaumer, London (GB); Oxana Polyakova, London (GB); Raj Mehta, London (GB); Adrian Hayday, London (GB); Pierre Vantourout, London (GB); Iva Zlatareva, London (GB); Daisy Melandri, London (GB); Robin John Campbell Dart, London (GB); Adam Laing, London (GB)

(73) Assignee: King's College London and GammaDelta Therapeutics Limited, London (GB)

( * ) Notice: Subject to any disclaimer, the term of this patent is extended or adjusted under 35 U.S.C. 154(b) by 869 days.

(21) Appl. No.: 16/972,534

(22) PCT Filed: Jun. 5, 2019

(86) PCT No.: PCT/EP2019/064739
§ 371 (c)(1),
(2) Date: Dec. 4, 2020

(87) PCT Pub. No.: WO2019/234136
PCT Pub. Date: Dec. 12, 2019

(65) Prior Publication Data
US 2021/0246187 A1 Aug. 12, 2021

Related U.S. Application Data

(60) Provisional application No. 62/680,932, filed on Jun. 5, 2018.

(51) Int. Cl.
| | | |
|---|---|---|
| C07K 14/725 | (2006.01) |
| A23L 33/15 | (2016.01) |
| A23L 33/18 | (2016.01) |
| A61K 31/4164 | (2006.01) |
| A61K 31/43 | (2006.01) |
| A61K 31/437 | (2006.01) |
| A61K 31/4709 | (2006.01) |
| A61K 31/496 | (2006.01) |
| A61K 31/52 | (2006.01) |
| A61K 31/573 | (2006.01) |
| A61K 31/606 | (2006.01) |
| A61K 38/18 | (2006.01) |
| A61K 38/20 | (2006.01) |
| A61K 45/06 | (2006.01) |
| C07K 16/24 | (2006.01) |
| C07K 16/28 | (2006.01) |

(52) U.S. Cl.
CPC .......... *C07K 14/7051* (2013.01); *A23L 33/15* (2016.08); *A23L 33/18* (2016.08); *A61K 31/4164* (2013.01); *A61K 31/43* (2013.01); *A61K 31/437* (2013.01); *A61K 31/4709* (2013.01); *A61K 31/496* (2013.01); *A61K 31/52* (2013.01); *A61K 31/573* (2013.01); *A61K 31/606* (2013.01); *A61K 38/1841* (2013.01); *A61K 38/2066* (2013.01); *A61K 45/06* (2013.01); *C07K 16/241* (2013.01); *C07K 16/244* (2013.01); *C07K 16/2803* (2013.01); *C07K 16/2839* (2013.01); *C07K 2317/565* (2013.01)

(58) Field of Classification Search
CPC ............ C07K 14/7051; C07K 16/2803; C07K 2317/565
See application file for complete search history.

(56) References Cited

FOREIGN PATENT DOCUMENTS

| | | |
|---|---|---|
| CN | 102295702 A | 12/2011 |
| CN | 105296431 A | 2/2016 |
| CN | 107630085 A | 1/2018 |
| WO | WO-2011/127141 A1 | 10/2011 |
| WO | WO 2014/015148 A1 | 1/2014 |
| WO | WO-2016/037985 A1 | 3/2016 |

OTHER PUBLICATIONS

Jiang, Y., et al., "Flanking V and J sequences of complementary determining region 3 of T cell receptor (TCR) δ1 (CDR3δ1) determine the structure and function of TCRγ4δ1," J Biol Chem 286(29):25611-25619, American Society for Biochemistry and Molecular Biology, United States (Jul. 2011).

Willcox, C.R., et al., "Cytomegalovirus and tumor stress surveillance by binding of a human γδ T cell antigen receptor to endothelial protein C receptor," Nat Immunol 13(9):872-879, Nature Portfolio, United States (Sep. 2012).

Abeler-Dörner, L. et al., "Butyrophilins: An Emerging Family of Immune Regulators," Trends in Immunology, vol. 33, No. 1, Jan. 2012, pp. 34-41.

Arnett, H. et al., "Immune modulation by butyrophilins," Nature Reviews | Immunology, vol. 14, Aug. 2014, pp. 559-569.

(Continued)

*Primary Examiner* — Elly-Gerald Stoica
(74) *Attorney, Agent, or Firm* — Sterne, Kessler, Goldstein & Fox P.L.L.C.

(57) ABSTRACT

Protein constructs comprising a BTNL3/8 targeting moiety, a payload and an optional linker are described herein. Pharmaceutical compositions comprising the constructs, and methods of use thereof are presented.

15 Claims, 20 Drawing Sheets

Specification includes a Sequence Listing.

(56) References Cited

OTHER PUBLICATIONS

Dart, R. et al., "Normality-Sensing in the Human Gut: Epithelial Butyrophilin-Like Proteins 3 and 8 Selectively Regulate an Abundant Subset of Human Colonic γδ T Cells at Steady-State", Gastroenterology 152(5), Apr. 2017, pp. S964-S965.

Di Marco Barros, R. et al., "Epithelia Use Butyrophilin-like Molecules to Shape Organ-Specific γδ T Cell Compartments," Cell, vol. 1667, Iss. 1, Sep. 22, 2016, pp. 203-218e17.

The Human Protein Atlas, "Tissue expression of BTNL8," Date Unknown, two pages, [Online] [Retrieved on Mar. 3, 2021] Retrieved from the Internet <URL: https://www.proteinatlas.org/ENSG00000113303-BTNL8/tissue>.

The Human Protein Atlas, "Tissue expression of BTNL3," Date Unknown, two pages, [Online] [Retrieved on Mar. 3, 2021] Retrieved from the Internet <URL: https://www.proteinatlas.org/ENSG00000168903-BTNL3/tissue>.

"Human T cell receptor alpha chain, SEQ ID 3.", Geneseq12 Apr. 2012 (Apr. 12, 2012), retrieved from EBI accession No. GSP:AZT49871 Database accession No. AZT49871, XP002793600, one page.

Kabelitz, D. et al., "Immunosurveillance by human γδ T lymphocytes: the emerging role of butyrophilins [versions 1; referees: 2 approved]," F1000Research, Jun. 5, 2017, pp. 1-10.

Mayassi, T. et al., "Chronic Inflammation Permanently Reshapes Tissue-Resident Immunity in Celiac Disease", Cell, vol. 176, No. 5, Feb. 1, 2019, pp. 967-981.e19.

Melandri, D. et al., "The γδTCR combines innate immunity with adaptive immunity by utilizing spatially distinct regions for agonist selection and antigen responsiveness," Nature Immunology, vol. 19, No. 12, Nov. 12, 2018, p. 1352-1365.

PCT International Search Report and Written Opinion, PCT Application No. PCT/EP2019/064739, Sep. 13, 2019, 14 pages.

Vantourout, P. et al., "Heteromeric interactions regulate butyrophilin (BTN) and BTN-like molecules governing γδ T cell biology," PNAS, vol. 115, No. 5, Jan. 16, 2018, pp. 1039-1044.

Xu, B. et al., "Crystal structure of a γδ T-cell receptor specific for the human MHC class I homolog MICA," PNAS, vol. 108, No. 6, Feb. 8, 2011, pp. 2414-2419.

Figure 1

Alignment of human Vγ4, human Vγ2 and mouse Vγ7 V regions

```
N-Terminus                                        CDR1                                    CDR2
  hVγ4        SSNLEGRTKSVIRQTGSSAEITCDLAEGSTGYIHWYLHQEGKAPQRLLYYDSYTSSVVLE
  hVγ2        SSNLEGRTKSVIRQTGSSAEITCDLAEGSNGYIHWYLHQEGKAPQRLQYYDSYNSKVVLE
  mVγ7        SSNLEERIMSITKLEGSSAIMTCDTHR-TGTYIHWYRFQKGRAPEHLLYYNFVSSTTVVD
                        *                                                          *
Amino Acid Position 19      25       30       35       40       45       50       55       60       65       70       75    78
                                                                                                        C-Terminus
                           CDR4/HV4                                      CDR3
  hVγ4        SGISPGKYDTYGSTRKNLRMILRNLIENDSGVYYCATWDG
  hVγ2        SGVSPGKYYTYASTRNNLRLILRNLIENDSGVYYCATWDG
  mVγ7        SRFNSEKYHVYEGPDKRYKFVLRNVEESDSALYYCASWA-
                                                     *
Amino Acid Position 79      85       90       95       100      105      110      115
```

Lentiviral vector backbone used for expression (custom-designed)

Example of TCR transduction in the Jurkat-derived TCRαβ-/- cell line J76 (72h post-transduction)

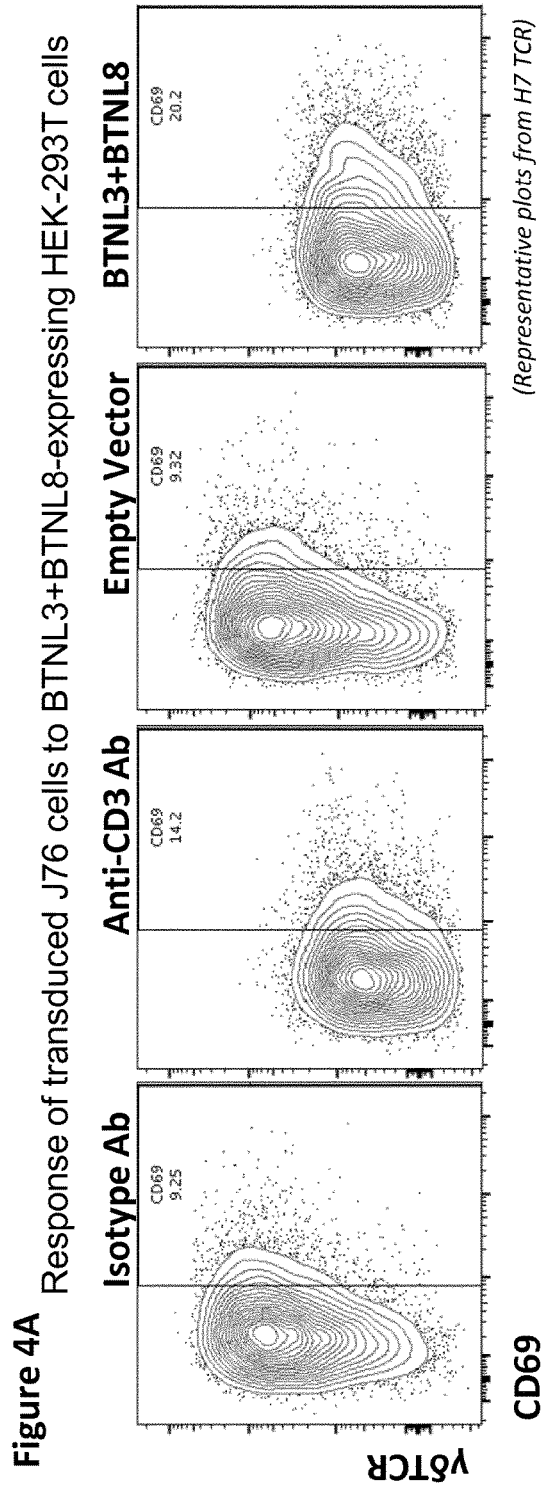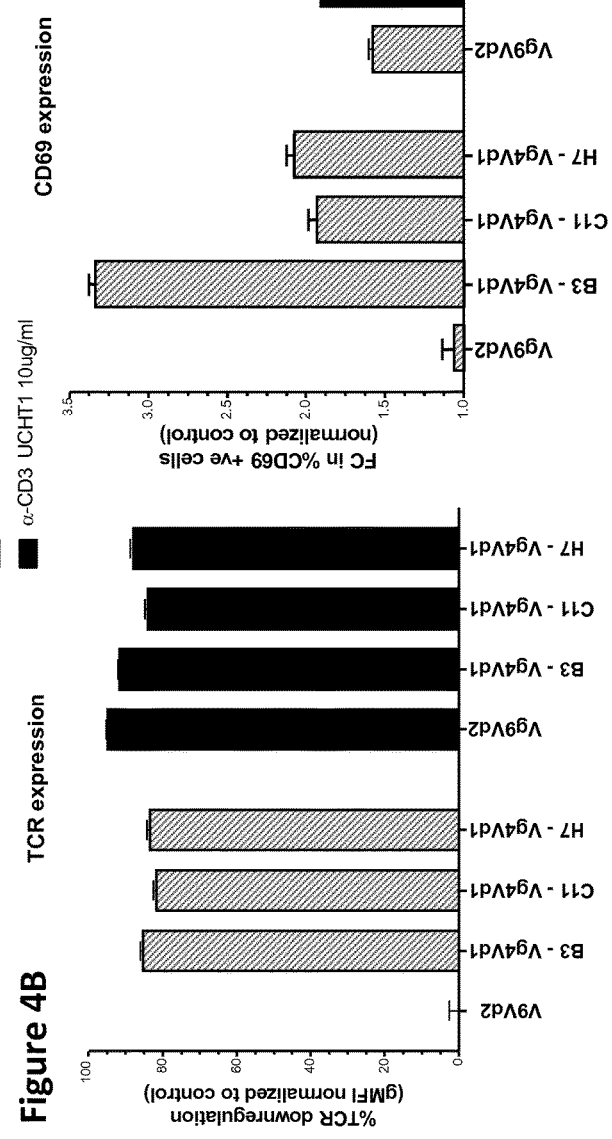
Figure 4A. Response of transduced J76 cells to BTNL3+BTNL8-expressing HEK-293T cells
Figure 4B.

```
TRGV2  SSNLEGRTKSVIRQTGSSAEITCDLAEGSNGY IHWYLHQEGKAPQRLQYYDSYNSKVVLESGVSPGKYYTYASTRNNLRLIRNLIENDSGVYYCATWDG
TRGV4  SSNLEGRTKSVIRQTGSSAEITCDLAEGSTGY IHWYLHQEGKAPQRLLYYDSYTSSVVLESGISPGKYDTYGSTRKNLRMLRNLIENDSGVYYCATWDG
         CDR1                             CDR2                            "CDR4"                  CDR3
```

Structures from:
Luoma, Immunity 2013
Ulrich, Nat Immunol 2013

Cells stained with indicated soluble TCR constructs (His-tagged) + αHis-APC

*Numbers above plots indicate dilutions of the TCR + αHis-APC*

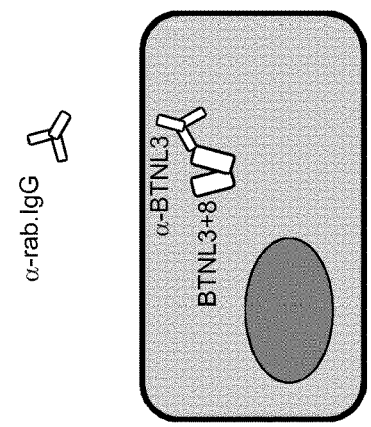
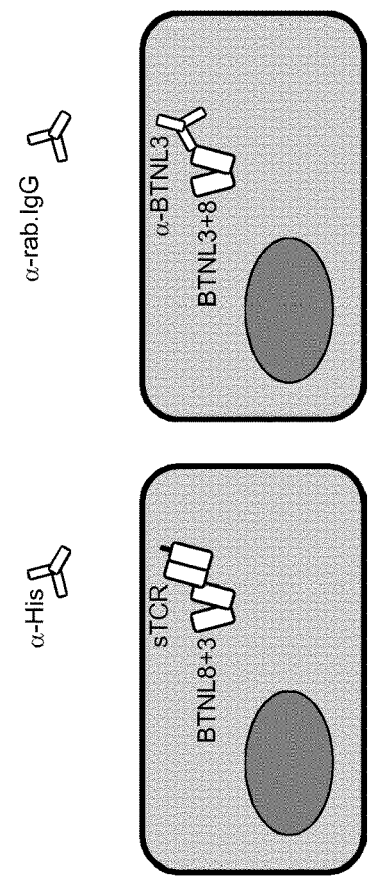
Figure 11B
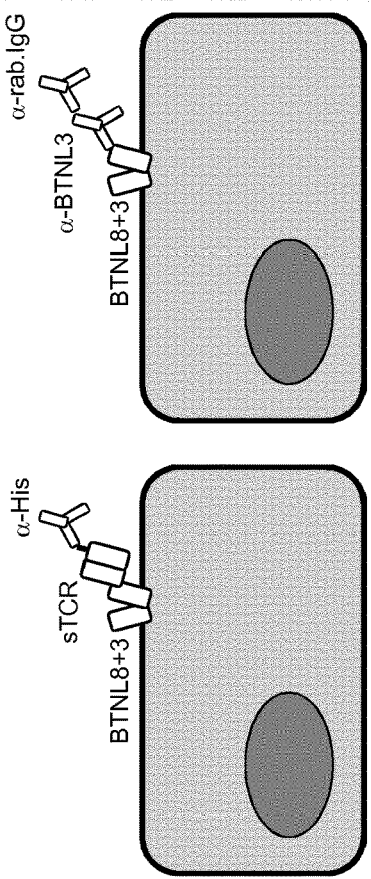
Figure 11A

SEQUENCE LISTING

```
<160> NUMBER OF SEQ ID NOS: 18

<210> SEQ ID NO 1
<211> LENGTH: 4
<212> TYPE: PRT
<213> ORGANISM: Homo sapiens

<400> SEQUENCE: 1

Asp Thr Tyr Gly
1

<210> SEQ ID NO 2
<211> LENGTH: 4
<212> TYPE: PRT
<213> ORGANISM: Mus sp.

<400> SEQUENCE: 2

His Val Tyr Glu
1

<210> SEQ ID NO 3
<211> LENGTH: 16
<212> TYPE: PRT
<213> ORGANISM: Homo sapiens

<400> SEQUENCE: 3

Lys Tyr Asp Thr Tyr Gly Ser Thr Arg Lys Asn Leu Arg Met Ile Leu
1               5                   10                  15

<210> SEQ ID NO 4
<211> LENGTH: 16
<212> TYPE: PRT
<213> ORGANISM: Mus sp.

<400> SEQUENCE: 4
```

```
Lys Tyr His Val Tyr Glu Gly Pro Asp Lys Arg Tyr Lys Phe Val Leu
1               5                   10                  15
```

<210> SEQ ID NO 5
<211> LENGTH: 16
<212> TYPE: PRT
<213> ORGANISM: Homo sapiens

<400> SEQUENCE: 5

```
Lys Tyr Tyr Thr Tyr Ala Ser Thr Arg Asn Asn Leu Arg Leu Ile Leu
1               5                   10                  15
```

<210> SEQ ID NO 6
<211> LENGTH: 100
<212> TYPE: PRT
<213> ORGANISM: Homo sapiens

<400> SEQUENCE: 6

```
Ser Ser Asn Leu Glu Gly Arg Thr Lys Ser Val Ile Arg Gln Thr Gly
1               5                   10                  15

Ser Ser Ala Glu Ile Thr Cys Asp Leu Ala Glu Gly Ser Thr Gly Tyr
                20                  25                  30

Ile His Trp Tyr Leu His Gln Glu Gly Lys Ala Pro Gln Arg Leu Leu
            35                  40                  45

Tyr Tyr Asp Ser Tyr Thr Ser Ser Val Val Leu Glu Ser Gly Ile Ser
50                  55                  60

Pro Gly Lys Tyr Asp Thr Tyr Gly Ser Thr Arg Lys Asn Leu Arg Met
65                  70                  75                  80

Ile Leu Arg Asn Leu Ile Glu Asn Asp Ser Gly Val Tyr Tyr Cys Ala
                85                  90                  95

Thr Trp Asp Gly
            100
```

<210> SEQ ID NO 7
<211> LENGTH: 100
<212> TYPE: PRT
<213> ORGANISM: Homo sapiens

<400> SEQUENCE: 7

```
Ser Ser Asn Leu Glu Gly Arg Thr Lys Ser Val Ile Arg Gln Thr Gly
1               5                   10                  15

Ser Ser Ala Glu Ile Thr Cys Asp Leu Ala Glu Gly Ser Asn Gly Tyr
                20                  25                  30

Ile His Trp Tyr Leu His Gln Glu Gly Lys Ala Pro Gln Arg Leu Gln
            35                  40                  45

Tyr Tyr Asp Ser Tyr Asn Ser Lys Val Val Leu Glu Ser Gly Val Ser
50                  55                  60

Pro Gly Lys Tyr Tyr Thr Tyr Ala Ser Thr Arg Asn Asn Leu Arg Leu
65                  70                  75                  80

Ile Leu Arg Asn Leu Ile Glu Asn Asp Ser Gly Val Tyr Tyr Cys Ala
                85                  90                  95

Thr Trp Asp Gly
            100
```

<210> SEQ ID NO 8
<211> LENGTH: 98
<212> TYPE: PRT
<213> ORGANISM: Mus sp.

<400> SEQUENCE: 8

Ser Ser Asn Leu Glu Glu Arg Ile Met Ser Ile Thr Lys Leu Glu Gly
1               5                   10                  15

Ser Ser Ala Ile Met Thr Cys Asp Thr His Arg Thr Gly Thr Tyr Ile
            20                  25                  30

His Trp Tyr Arg Phe Gln Lys Gly Arg Ala Pro Glu His Leu Leu Tyr
        35                  40                  45

Tyr Asn Phe Val Ser Ser Thr Thr Val Val Asp Ser Arg Phe Asn Ser
    50                  55                  60

Glu Lys Tyr His Val Tyr Glu Gly Pro Asp Lys Arg Tyr Lys Phe Val
65                  70                  75                  80

Leu Arg Asn Val Glu Glu Ser Asp Ser Ala Leu Tyr Tyr Cys Ala Ser
                85                  90                  95

Trp Ala

<210> SEQ ID NO 9
<211> LENGTH: 254
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Ala Gln Lys Val Thr Gln Ala Gln Ser Ser Val Ser Met Pro Val Arg
1               5                   10                  15

Lys Ala Val Thr Leu Asn Cys Leu Tyr Glu Thr Ser Trp Trp Ser Tyr
            20                  25                  30

Tyr Ile Phe Trp Tyr Lys Gln Leu Pro Ser Lys Glu Met Ile Phe Leu
        35                  40                  45

Ile Arg Gln Gly Ser Asp Glu Gln Asn Ala Lys Ser Gly Arg Tyr Ser
    50                  55                  60

Val Asn Phe Lys Lys Ala Ala Lys Ser Val Ala Leu Thr Ile Ser Ala
65                  70                  75                  80

Leu Gln Leu Glu Asp Ser Ala Lys Tyr Phe Cys Ala Leu Gly Glu Ser
                85                  90                  95

Leu Thr Arg Ala Asp Lys Leu Ile Phe Gly Lys Gly Thr Arg Val Thr
                100                 105                 110

Val Glu Pro Asn Ile Gln Asn Pro Asp Pro Ala Val Tyr Gln Leu Arg
            115                 120                 125

Asp Ser Lys Ser Ser Asp Lys Ser Val Cys Leu Phe Thr Asp Phe Asp
130                 135                 140

Ser Gln Thr Asn Val Ser Gln Ser Lys Asp Ser Asp Val Tyr Ile Thr
145                 150                 155                 160

Asp Lys Thr Val Leu Asp Met Arg Ser Met Asp Phe Lys Ser Asn Ser
                165                 170                 175

Ala Val Ala Trp Ser Asn Lys Ser Asp Phe Ala Cys Ala Asn Ala Phe
            180                 185                 190

Asn Asn Ser Ile Ile Pro Glu Asp Thr Phe Phe Pro Ser Pro Glu Ser
        195                 200                 205

Ser Cys Thr Thr Ala Pro Ser Ala Gln Leu Lys Lys Lys Leu Gln Ala
    210                 215                 220

Leu Lys Lys Lys Asn Ala Gln Leu Lys Trp Lys Leu Gln Ala Leu Lys
225                 230                 235                 240

Lys Lys Leu Ala Gln Gly Ser Gly His His His His His His

-continued

```
                245                 250

<210> SEQ ID NO 10
<211> LENGTH: 270
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Ser Ser Asn Leu Glu Gly Arg Thr Lys Ser Val Ile Arg Gln Thr Gly
1               5                   10                  15

Ser Ser Ala Glu Ile Thr Cys Asp Leu Ala Glu Gly Ser Thr Gly Tyr
            20                  25                  30

Ile His Trp Tyr Leu His Gln Glu Gly Lys Ala Pro Gln Arg Leu Leu
        35                  40                  45

Tyr Tyr Asp Ser Tyr Thr Ser Ser Val Val Leu Glu Ser Gly Ile Ser
    50                  55                  60

Pro Gly Lys Tyr Asp Thr Tyr Gly Ser Thr Arg Lys Asn Leu Arg Met
65                  70                  75                  80

Ile Leu Arg Asn Leu Ile Glu Asn Asp Ser Gly Val Tyr Tyr Cys Ala
                85                  90                  95

Thr Trp Asp Glu Lys Tyr Tyr Lys Lys Leu Phe Gly Ser Gly Thr Thr
            100                 105                 110

Leu Val Val Thr Glu Asp Leu Lys Asn Val Phe Pro Pro Glu Val Ala
        115                 120                 125

Val Phe Glu Pro Ser Glu Ala Glu Ile Ser His Thr Gln Lys Ala Thr
    130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Gly Val Ser Thr Asp Pro
                165                 170                 175

Gln Pro Leu Lys Glu Gln Pro Ala Leu Asn Asp Ser Arg Tyr Ala Leu
            180                 185                 190

Ser Ser Arg Leu Arg Val Ser Ala Thr Phe Trp Gln Asn Pro Arg Asn
        195                 200                 205

His Phe Arg Cys Gln Val Gln Phe Tyr Gly Leu Ser Glu Asn Asp Glu
    210                 215                 220

Trp Thr Gln Asp Arg Ala Lys Pro Val Thr Gln Ile Val Ser Ala Glu
225                 230                 235                 240

Ala Trp Gly Arg Ala Asp Cys Thr Thr Ala Pro Ser Ala Gln Leu Glu
                245                 250                 255

Lys Glu Leu Gln Ala Leu Glu Lys Glu Asn Ala Gln Leu Glu
            260                 265                 270

<210> SEQ ID NO 11
<211> LENGTH: 255
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Ala Ile Glu Leu Val Pro Glu His Gln Thr Val Pro Val Ser Ile Gly
1               5                   10                  15
```

Val Pro Ala Thr Leu Arg Cys Ser Met Lys Gly Glu Ala Ile Gly Asn
            20                  25                  30

Tyr Tyr Ile Asn Trp Tyr Arg Lys Thr Gln Gly Asn Thr Ile Thr Phe
        35                  40                  45

Ile Tyr Arg Glu Lys Asp Ile Tyr Gly Pro Gly Phe Lys Asp Asn Phe
50                  55                  60

Gln Gly Asp Ile Asp Ile Ala Lys Asn Leu Ala Val Leu Lys Ile Leu
65                  70                  75                  80

Ala Pro Ser Glu Arg Asp Glu Gly Ser Tyr Tyr Cys Ala Leu Gly Glu
                85                  90                  95

Ser Leu Thr Arg Ala Asp Lys Leu Ile Phe Gly Lys Gly Thr Arg Val
            100                 105                 110

Thr Val Glu Pro Asn Ile Gln Asn Pro Asp Pro Ala Val Tyr Gln Leu
        115                 120                 125

Arg Asp Ser Lys Ser Ser Asp Lys Ser Val Cys Leu Phe Thr Asp Phe
130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
        195                 200                 205

Ser Ser Cys Thr Thr Ala Pro Ser Ala Gln Leu Lys Lys Lys Leu Gln
210                 215                 220

Ala Leu Lys Lys Lys Asn Ala Gln Leu Lys Trp Lys Leu Gln Ala Leu
225                 230                 235                 240

Lys Lys Lys Leu Ala Gln Gly Ser Gly His His His His His His
                245                 250                 255

<210> SEQ ID NO 12
<211> LENGTH: 282
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Ser Ser Asn Leu Glu Gly Arg Thr Lys Ser Val Ile Arg Gln Thr Gly
1               5                   10                  15

Ser Ser Ala Glu Ile Thr Cys Asp Leu Ala Glu Gly Ser Asn Gly Tyr
            20                  25                  30

Ile His Trp Tyr Leu His Gln Glu Gly Lys Ala Pro Gln Arg Leu Gln
        35                  40                  45

Tyr Tyr Asp Ser Tyr Asn Ser Lys Val Val Leu Glu Ser Gly Val Ser
    50                  55                  60

Pro Gly Lys Tyr Tyr Thr Tyr Ala Ser Thr Arg Asn Asn Leu Arg Leu
65                  70                  75                  80

Ile Leu Arg Asn Leu Ile Glu Asn Asp Ser Gly Val Tyr Tyr Cys Ala
                85                  90                  95

Thr Trp Asp Glu Lys Tyr Tyr Lys Lys Leu Phe Gly Ser Gly Thr Thr
            100                 105                 110

```
Leu Val Val Thr Glu Asp Leu Lys Asn Val Phe Pro Pro Glu Val Ala
            115                 120                 125

Val Phe Glu Pro Ser Glu Ala Glu Ile Ser His Thr Gln Lys Ala Thr
        130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Gly Val Ser Thr Asp Pro
                165                 170                 175

Gln Pro Leu Lys Glu Gln Pro Ala Leu Asn Asp Ser Arg Tyr Ala Leu
            180                 185                 190

Ser Ser Arg Leu Arg Val Ser Ala Thr Phe Trp Gln Asn Pro Arg Asn
        195                 200                 205

His Phe Arg Cys Gln Val Gln Phe Tyr Gly Leu Ser Glu Asn Asp Glu
    210                 215                 220

Trp Thr Gln Asp Arg Ala Lys Pro Val Thr Gln Ile Val Ser Ala Glu
225                 230                 235                 240

Ala Trp Gly Arg Ala Asp Cys Thr Thr Ala Pro Ser Ala Gln Leu Glu
                245                 250                 255

Lys Glu Leu Gln Ala Leu Glu Lys Glu Asn Ala Gln Leu Glu Trp Glu
            260                 265                 270

Leu Gln Ala Leu Glu Lys Glu Leu Ala Gln
        275                 280
```

<210> SEQ ID NO 13
<211> LENGTH: 282
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 13

```
Ser Ser Asn Leu Glu Gly Arg Thr Lys Ser Val Thr Arg Pro Thr Gly
1               5                   10                  15

Ser Ser Ala Val Ile Thr Cys Asp Leu Pro Val Glu Asn Ala Val Tyr
            20                  25                  30

Thr His Trp Tyr Leu His Gln Glu Gly Lys Ala Pro Gln Arg Leu Leu
        35                  40                  45

Tyr Tyr Asp Ser Tyr Asn Ser Arg Val Val Leu Glu Ser Gly Ile Ser
    50                  55                  60

Arg Glu Lys Tyr His Thr Tyr Ala Ser Thr Gly Lys Ser Leu Lys Phe
65                  70                  75                  80

Ile Leu Glu Asn Leu Ile Glu Arg Asp Ser Gly Val Tyr Tyr Cys Ala
                85                  90                  95

Thr Trp Asp Glu Lys Tyr Tyr Lys Leu Phe Gly Ser Gly Thr Thr
                100                 105                 110

Leu Val Val Thr Glu Asp Leu Lys Asn Val Phe Pro Pro Glu Val Ala
            115                 120                 125

Val Phe Glu Pro Ser Glu Ala Glu Ile Ser His Thr Gln Lys Ala Thr
        130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Gly Val Ser Thr Asp Pro
                165                 170                 175

Gln Pro Leu Lys Glu Gln Pro Ala Leu Asn Asp Ser Arg Tyr Ala Leu
```

```
                180                 185                 190
Ser Ser Arg Leu Arg Val Ser Ala Thr Phe Trp Gln Asn Pro Arg Asn
            195                 200                 205
His Phe Arg Cys Gln Val Gln Phe Tyr Gly Leu Ser Glu Asn Asp Glu
        210                 215                 220
Trp Thr Gln Asp Arg Ala Lys Pro Val Thr Gln Ile Val Ser Ala Glu
225                 230                 235                 240
Ala Trp Gly Arg Ala Asp Cys Thr Thr Ala Pro Ser Ala Gln Leu Glu
                245                 250                 255
Lys Glu Leu Gln Ala Leu Glu Lys Glu Asn Ala Gln Leu Glu Trp Glu
            260                 265                 270
Leu Gln Ala Leu Glu Lys Glu Leu Ala Gln
        275                 280
```

```
<210> SEQ ID NO 14
<211> LENGTH: 18
<212> TYPE: PRT
<213> ORGANISM: Homo sapiens

<400> SEQUENCE: 14

Met Ala Trp Ala Leu Ala Val Leu Leu Ala Phe Leu Ser Pro Ala Ser
1               5                   10                  15

Gln Lys

<210> SEQ ID NO 15
<211> LENGTH: 20
<212> TYPE: PRT
<213> ORGANISM: Homo sapiens

<400> SEQUENCE: 15

Gly Gln Glu Leu Gly Lys Lys Ile Lys Val Phe Gly Pro Gly Thr Lys
1               5                   10                  15

Leu Ile Ile Thr
            20

<210> SEQ ID NO 16
<211> LENGTH: 20
<212> TYPE: PRT
<213> ORGANISM: Homo sapiens

<400> SEQUENCE: 16

Gly Gln Glu Leu Gly Lys Lys Ile Lys Val Phe Gly Pro Gly Thr Lys
1               5                   10                  15

Leu Ile Ile Thr
            20

<210> SEQ ID NO 17
<211> LENGTH: 19
<212> TYPE: PRT
<213> ORGANISM: Homo sapiens

<400> SEQUENCE: 17

Ser Ser Asp Trp Ile Lys Thr Phe Ala Lys Gly Thr Arg Leu Ile Val
1               5                   10                  15

Thr Ser Pro

<210> SEQ ID NO 18
<211> LENGTH: 16
<212> TYPE: PRT
<213> ORGANISM: Homo sapiens
```

```
<400> SEQUENCE: 18

Asn Tyr Tyr Lys Lys Leu Phe Gly Ser Gly Thr Thr Leu Val Val Thr
1               5                   10                  15
```

BTNL3/8 TARGETING CONSTRUCTS FOR DELIVERY OF PAYLOADS

1. CROSS-REFERENCE TO RELATED APPLICATIONS

This application claims the benefit of U.S. Provisional Application No. 62/680,932 filed Jun. 5, 2018, which is hereby incorporated by reference in its entirety.

2. SEQUENCE LISTING

The instant application contains a Sequence Listing which has been submitted via EFS-Web and is hereby incorporated herein by reference in its entirety. Said ASCII copy, created on Jun. 4, 2019, is named GDT-P2577PCT—sequence listing.txt, and is 17,284 bytes in size.

3. BACKGROUND

Most drugs rely on systemic exposure to achieve sufficient concentration at the pathological site. However, exposure of the agent to off-target tissues frequently results in significant toxicity. Hence, there is an urgent need for development of methods for delivering pharmaceutical agents to specific tissues.

Tissue-selective homing of T cells is considered a critical element during the integration of normal immune responses. One interesting and highly unique class of such 'tissue homing' or 'tissue resident' T cells are γδ T cells. γδ T cells are heavily compartmentalized T cells that show localization of subsets to specific tissues, e.g., murine Vγ5 T cells are only found in the epidermis whilst murine Vγ7 T cells are unique to the intestine. Several murine and human IEL compartments depend for their development and survival on proteins expressed by epithelial cells at steady state such as Butyrophilins (BTN) and Butyrophilin-like (Btnl/BTNL) genes, via as-yet unelucidated mechanisms. (Di Marco Barros et al., Cell. 2016; 167(1): 203-218; Kabelitz et al., F1000 Faculty Rev: 782; Jun. 5, 2017).

The butyrophilin and butyrophilin-like proteins (BTN/BTNL) are a family of immunoglobulin superfamily members that influence immunity, such as T cell selection, as well as developmental processes, such as differentiation and cell fate determination (Arnett and Viney, Nature Reviews, 2014 (14) pp. 559-569). It has been shown that BTNL proteins (specifically, BTNL3 and BTNL8) are disproportionally highly expressed in human intestinal enterocytes, and that BTNL3/8 can specifically modulate human Vγ4+γδ T cells (Di Marco Barros et al., Cell. 2016; 167(1): 203-218). Whereas BTN and BTNL proteins are reported to regulate multiple T-cell responses in a negative or positive manner, it is not clear how such signals are transmitted to T Cells (Kabelitz et al., F1000 Faculty Rev: 782; Jun. 5, 2017).

There is a need for localized delivery of agents to the gastrointestinal system for the treatment of diseases, such as inflammatory bowel diseases. There is, therefore, a need for compounds capable of targeting BTNL3/8 expressing cells, including compounds capable of targeting therapeutic payloads to BTNL3/8 expressing cells, in particular BTNL3/8 expressing cells of the intestinal epithelia.

4. SUMMARY

To further explore such remarkable—albeit poorly characterized—tissue/immune compartment 'shaping' and 'homing' further, we have attempted to explore the mechanisms by which γδ T cell tissue targeting and specificity is achieved. First, we attempted to engineer a panel of recombinant heterodimer and homodimer γδ T cell receptor proteins (TCR) from starting human γ chain and δ chain sequences. To achieve this, we explored a variety of fusion partners to ensure the resulting recombinant heterodimerized and homodimerized γδ chains are expressed (e.g., in HEK293 cells), remain intact, are predominantly free from aggregation (as measured by size exclusion chromatography) when purified. From these experiments, we identified a number of more preferable fusion partners including (i) the use of antibody Fc fusion domain partners and (ii) the use of TCR alpha-beta chain constant domain partners combined with engineered leucine zipper (Xu et al., PNAS, 2011 Vol. 108; pp. 2414-2419). However, given these successful experiments were non-exhaustive, we also appreciate others ordinarily skilled in the art will now be motivated to identify alternative approaches to generating recombinant γδ homodimers, heterodimers and monomer sub-units.

Once this panel or library of human γδ sequence derived T cell receptor recombinant proteins was created, we next used it to explore which recombinant γδ pairings (if any) exhibited any tissue specificity or selectivity. Accordingly, we incubated these proteins with a cell line over-expressing BTNL3/8. Unprecedentedly, through controlled studies we then identified certain recombinant T-cell receptors that specifically recognized BTNL3/8 protein (e.g., a recombinant γ4δ1 TCR and a recombinant γ4δ2 TCR) whilst we identified other such receptors that did not (e.g., a recombinant γ2δ1 TCR and a recombinant γ8δ1 TCR). This shows, for the first time, that γ4 containing γδ TCR directly interacts with BTNL3/8 expressed on a cell surface.

Furthermore, TCR deep sequencing showed that there was a selective enrichment of γ4 TCR expressing γδ T-cells in the fraction that was BTNL3/8-responsive. Collectively, the sequencing data and recombinant TCR experiments showed that TCR pairings containing the γ4 subunit bound selectively to BTNL3/8.

Accordingly, in a first aspect, a protein construct is provided. The protein construct comprises a BTNL3/8 targeting moiety, a payload, and an optional linker linking the targeting moiety to the payload.

In certain embodiments, the BTNL3/8 targeting moiety comprises a Vγ domain, wherein the amino acid at sequence position number 87 of the Vγ domain is aspartic acid or histidine and the amino acid at sequence position number 90 of the Vγ domain is glycine or glutamic acid, and wherein the remaining residues of the Vγ CDR4 are, at each position, independently selected from the corresponding residues of a human or murine Vγ domain.

In certain embodiments, the remaining residues of the Vγ domain CDR4 are, at each residue position, independently selected from the corresponding residues of human Vγ4, human Vγ2, or mouse Vγ7. In an embodiment, the amino acid sequence at positions numbers 87-90 of the Vγ domain is SEQ ID NO: 1. In an embodiment, the amino acid sequence at positions numbers 87-90 of the Vγ domain is SEQ ID NO: 2. In an embodiment, the remaining residues of the Vγ domain CDR4 are all selected from the corresponding residues of human Vγ4, human Vγ2, or mouse Vγ7. In an embodiment, the remaining residues of the Vγ CDR4 are selected from the corresponding residues of human Vγ4. In an embodiment, the remaining residues of the Vγ CDR4 are selected from the corresponding residues of human Vγ2. In an embodiment, the remaining residues of the Vγ CDR4 are selected from the corresponding residues of mouse Vγ7. In an embodiment, the Vγ domain is a human Vγ2 domain in which the amino acids of the CDR4 are substituted with aspartic acid or histidine at amino acid sequence position number 87 and substituted with glycine or glutamic acid at amino acid sequence position number 90. In an embodiment, the Vγ domain is a human Vγ4 domain.

In an embodiment, the Vγ domain CDR3 is a human or mouse Vγ CDR3 sequence. In an embodiment, the Vγ domain CDR3 comprises a human Vγ4 CDR3 sequence. In an embodiment, the Vγ domain CDR3 comprises a human Vγ2 CDR3 sequence. In an embodiment, the Vγ domain CDR3 comprises a mouse Vγ7 CDR3 sequence. In an embodiment, the J region is a Vγ J region In an embodiment, the J region is a mouse Vγ J region. In certain embodiments, the J region comprises a SEQ ID NO selected from the group consisting of SEQ ID NOs: 15-18.

In certain embodiments, the BTNL3/8 targeting moiety of the protein construct further comprises a paired Vδ domain. In an embodiment, the Vγ domain and the Vδ domain are covalently linked by at least one disulfide bond. In an embodiment, the Vγ domain and the Vδ domain are paired by a specific heterodimeric interaction. In an embodiment, the heterodimeric interaction is leucine zipper complementarity. In an embodiment, the targeting moiety comprises SEQ ID NO: 9. In an embodiment, the targeting moiety is SEQ ID NO: 10. In an embodiment, the targeting moiety is SEQ ID NO: 11. In an embodiment, the targeting moiety comprises a single chain in-frame fusion of the Vγ domain and the Vδ domain. In an embodiment, the Vγ domain is N terminal to the V6 domain. In an embodiment, the Vγ domain is C terminal to the Vδ domain. In an embodiment, the single chain in-frame fusion of the Vγ domain and the Vδ domain comprises an internal linker sequence. In an embodiment, Vδ domain is a human Vδ domain. In an embodiment, the human Vδ domain is Vδ1, Vδ2 or Vδ5. In an embodiment, the human Vδ domain is V1.

In certain embodiments, the protein construct further comprises a first T cell receptor constant region, wherein the first T cell receptor constant region is fused in-frame to the C terminus of the Vγ domain. In an embodiment, the first T cell receptor constant region is a human T cell receptor constant region. In an embodiment, the first T cell receptor constant region is a human T cell receptor β constant region. In an embodiment, the first T cell receptor constant region is a human T cell receptor α constant region. In an embodiment, the first T cell receptor constant region is a human T cell receptor γ constant region. In an embodiment, the targeting moiety further comprises a second T cell receptor constant region wherein the second T cell receptor constant region is fused in-frame to the C terminus of the paired Vδ domain. In an embodiment, the second T cell receptor constant region is a human T cell receptor α constant region. In an embodiment, the second T cell receptor constant region is a human T cell receptor β constant region. In an embodiment, the second T cell receptor constant region is a human T cell receptor δ constant region. In an embodiment, the in-frame fusion of the Vδ domain and the second T cell receptor constant region comprises an internal linker sequence between the Vδ domain and the second T cell receptor constant region.

In certain embodiments, the payload is a protein payload fused in frame to the targeting moiety. In an embodiment, the payload is a polypeptide. In an embodiment, the payload is a peptide. In an embodiment, the payload is a cytokine. In an embodiment, the payload is an antibody. In an embodiment, the payload is a single-chain variable fragment (scFv). In an embodiment, the antibody comprises at least an ABS specific for a cytokine antigen. In an embodiment, the antibody comprises at least an antigen binding site (ABS) specific for a CD3 antigen. In an embodiment, the antibody comprises at least an ABS specific for a Tumor Necrosis Factor alpha (TNFα) antigen. In an embodiment, the antibody comprises an Fc domain capable of interaction with Fc receptors. In an embodiment, the antibody comprises an Fc domain incapable of interaction with Fc receptors. In an embodiment, the payload is a small molecule. In an embodiment, the payload is a hormone. In an embodiment, the payload is a nucleic acid. In an embodiment, the payload is an inhibitory RNA (RNAi).

In certain embodiments, the optional linker is a peptide fused in-frame to the targeting moiety. In an embodiment, the optional linker is fused in frame to the C-terminus of the targeting moiety. In an embodiment, the optional linker is fused in frame to the N-terminus of the targeting moiety. In an embodiment, the optional linker is a molecule conjugated to the targeting moiety.

In certain aspects, described herein are pharmaceutical compositions comprising any one of the above mentioned protein constructs and a pharmaceutically acceptable carrier. In an embodiment, the pharmaceutical composition is suitable for parenteral administration. In an embodiment, the administration is intravenous administration. In an embodiment, the administration is intramuscular administration. In an embodiment, the administration is sub-cutaneous administration.

In certain aspects, described herein are methods of treating a condition of the gastrointestinal system in which gastrointestinal tissue expresses BTNL3/8, comprising: administering a therapeutically effective amount of a pharmaceutical composition to a patient with the condition in which the gastrointestinal tissue expresses BTNL3/8. In an embodiment of the method, the payload of the protein construct is an anti-inflammatory agent. In an embodiment, the anti-inflammatory agent is an aminosalicylate. In an embodiment, the anti-inflammatory agent is a non-steroidal anti-inflammatory agent. In an embodiment, the anti-inflammatory agent is an anti-inflammatory cytokine. In an embodiment, the anti-inflammatory agent is an anti-proinflammatory agent. In an embodiment, the anti-inflammatory agent is a steroid. In an embodiment, the steroid is a glucocorticoid. In an embodiment, the glucocorticoid is prednisone. In an embodiment, the glucocorticoid is hydrocortisone. In an embodiment, the payload is an immunomodulator.

In certain aspects, described herein are methods of treating an inflammatory bowel disease, comprising administering a therapeutically effective amount of any of the above mentioned pharmaceutical compositions to a patient with inflammatory bowel disease. In an embodiment, the inflammatory bowel disease is ulcerative colitis. In an embodiment, the inflammatory bowel disease is Crohn's disease. In an embodiment, the payload of the protein construct is an anti-inflammatory agent. In an embodiment, the anti-inflammatory agent is an aminosalicylate. In an embodiment, the anti-inflammatory agent is a non-steroidal anti-inflammatory. In an embodiment, the anti-inflammatory agent is an anti-inflammatory cytokine, optionally interleukin 10 (IL-10), interleukin 22 (IL-22) or Transforming Growth Factor Beta (TGFβ). In an embodiment, the anti-inflammatory agent payload is an anti-proinflammatory agent. In an embodiment, the anti-inflammatory agent payload is a steroid. In an embodiment, the steroid is a glucocorticoid. In an embodiment, the glucocorticoid is prednisone. In an embodiment, the glucocorticoid is hydrocortisone. In an embodiment, the payload of the protein construct is an antibiotic. In an embodiment, the antibiotic payload is rifaximin, ciprofloxacin, metronidazole, moxifloxacin or amoxicillin. In an embodiment, the payload of the protein construct is a calcineurin inhibitor. In an embodiment, the calcineurin inhibitor is cyclosporine A or tacrolimus. In an embodiment, the payload of the protein construct is an immunomodulator. In an embodiment, the immunomodulator is an immune suppressor. In an embodiment, the immune suppressor is azathioprine, 6-mercaptopurine, methotrexate or thiopurine. In an embodiment, the payload of the protein construct is a protein payload. In an embodiment, the protein payload is an antibody, an antibody fragment or a single chain variable fragment. In an embodiment, the protein payload comprises and at least an ABS specific for a TNFα antigen. In an embodiment, the protein payload comprises the complementarity-determining regions (CDRs) of adalimumab, infliximab or certolizumab. In an embodiment, the protein payload comprises at least an ABS specific for an interleukin antigen. In an embodiment, the interleukin is IL-12, IL-23, or combinations thereof. In an embodiment, the protein payload comprises the CDRs of ustekinumab or brikinumab. In an embodiment, the biologic payload comprises at least an ABS specific for an integrin antigen. In an embodiment, the integrin is alpha 4 integrin. In an embodiment, the protein payload comprises the CDRs of infliximab, natalizumab or vedolizumab. In an embodiment, the protein construct comprises an analgesic payload. In an embodiment, the protein construct comprises a dietary supplement payload.

In certain aspects, described herein are methods of treating irritable bowel syndrome, comprising administering a therapeutically effective amount of any one of the above mentioned pharmaceutical compositions to a patient with irritable bowel syndrome. In aspects embodiments, described herein are methods of treating diverticulitis, comprising administering a therapeutically effective amount of any one of the above mentioned pharmaceutical compositions to a patient with diverticulitis. In certain embodiments, the payload is an antibiotic. In certain embodiments, the antibiotic payload is rifaximin, ciprofloxacin, metronidazole, moxifloxacin or amoxicillin.

In certain aspects, described herein are methods of treating celiac disease, comprising administering a therapeutically effective amount of any one of the above mentioned pharmaceutical compositions to a patient with celiac disease. In certain embodiments, the payload is an immune suppressor. In certain embodiments, the immune suppressor is azathioprine, 6-mercaptopurine, methotrexate or thiopurine.

In certain aspects, described herein are methods of treating a microbial infection, comprising administering a therapeutically effective amount of any one of the above mentioned pharmaceutical compositions to a patient with the microbial infection. In certain embodiments, the payload is an anti-microbial agent. In certain embodiments, the anti-microbial agent is an anti-parasitic agent, an antibiotic, an anti-fungal agent or an anti-viral agent.

In certain aspects, described herein are methods of treating a metabolic disorder or metabolic deficiency, comprising administering a therapeutically effective amount of any one of the above mentioned pharmaceutical compositions to a patient with the metabolic disorder or metabolic deficiency. In certain embodiments, the payload is a dietary supplement. In certain embodiments, the dietary supplement is an enzyme or a vitamin.

In certain aspects, described herein are methods of modulating the immune system, comprising administering a therapeutically effective amount of any one of the above mentioned pharmaceutical compositions to a patient with an immune-related condition. In certain embodiments, the payload is an immune suppressor. In certain embodiments, the immune suppressor is azathioprine, 6-mercaptopurine, methotrexate or thiopurine. In certain embodiments, the payload is an immune stimulator. In certain embodiments, the immune stimulator is a cytokine.

5. BRIEF DESCRIPTION OF THE DRAWINGS

FIG. 1 shows an amino acid sequence alignment of human Vγ4 (hVγ4), human Vγ2 (hVγ2) and mouse Vγ7 (mVγ7) variable (V) domains. The amino acid position numbering shown here is based on the entire protein sequence of the T Cell Receptor (TCR), including the 18 amino acid leader sequence (not shown). The dashes at positions 46 and 117 in the alignment indicate gaps in the mVγ7 sequence introduced to optimize alignment. The CDR regions are indicated with boldface type font. CDR1 is located at amino acid positions 45-50 in the alignment. CDR2 is located at amino acid positions 68-75 in the alignment. The first 5 amino acids of the CDR3 are located at amino acid positions 114-118 in the alignment. CDR4 is located at amino acid positions 85-100 in the alignment. The underlined amino acids in human Vγ4-CDR4 at positions 87 and 90 in the alignment, when replaced with the corresponding amino acids in hVγ2, abrogated function (shown in FIG. 7).

FIG. 4A shows a representative example of the BTNL3/8-induced response of Vγ4VS1-transduced J76 cells. Positive control with anti-CD3 stimulation is also shown (vs. isotype control).

FIG. 4B shows that three independent Vγ4VS1-transduced J76 lines, but not a Vγ9Vδ2 line, responded to BTNL3/8-expressing cells. B3, C11 and H7 represent three different CDR3 pairs obtained with the method shown in FIG. 2.

Figure 5:
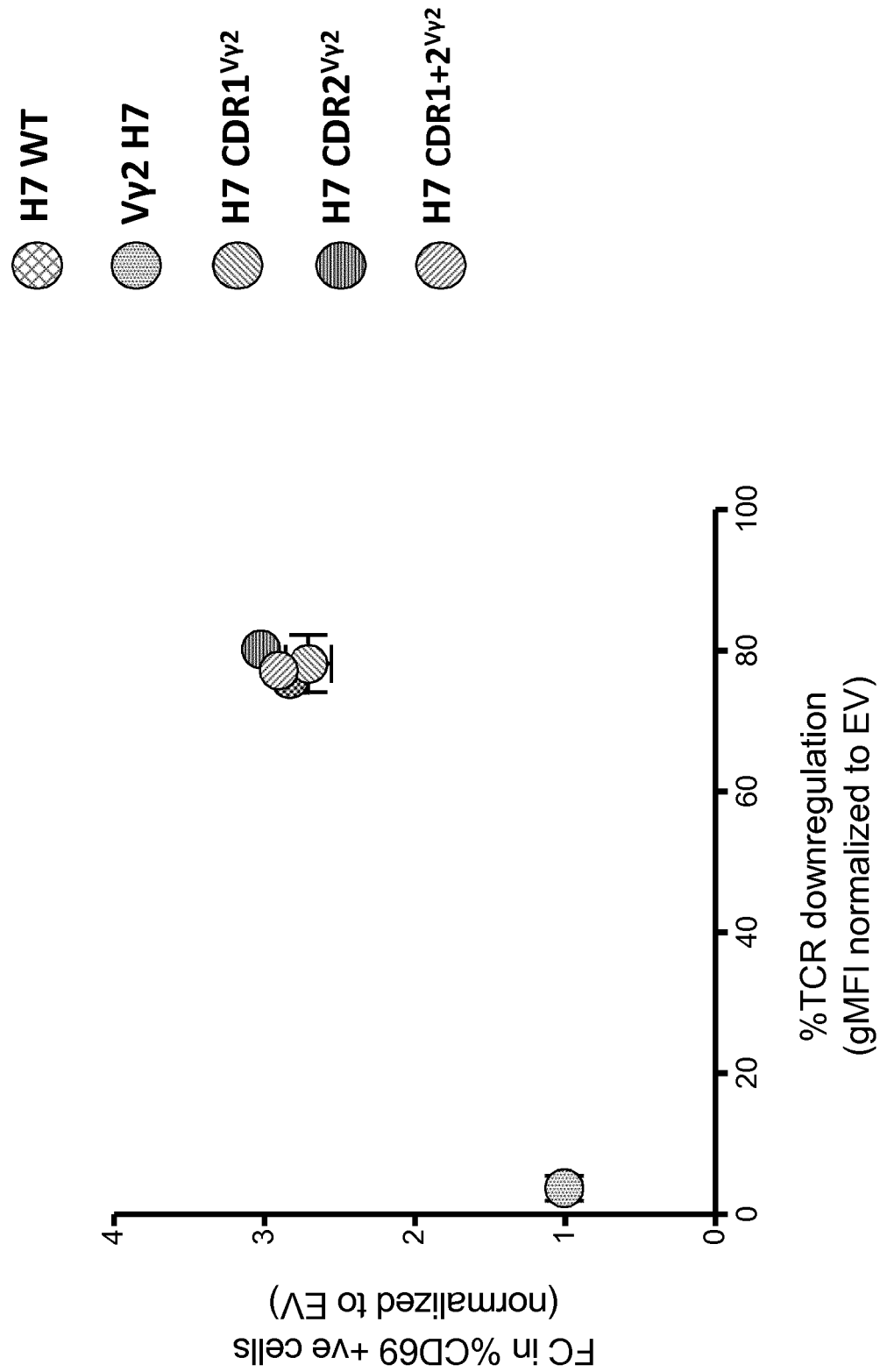

FIG. 5 shows the fold change (FC) in % CD69 expression in transduced cells (+ve cells) normalized to cells expressing empty vector (EV) and the percent TCR downregulation in J76 cells expressing Vγ4 TCR or Vγ2 TCR. When the full V domain of the responding Vγ4 H7 TCR was replaced by a Vγ2-coding sequence (Vγ2 H7) (CDR3gamma and full delta chain not replaced), TCR activation by the BTNL3/8 expressing cells was lost. However, when the CDR1 (H7 CDR1$^{Vγ2}$) and/or the CDR2 (H7 CDR2$^{Vγ2}$) of the responding Vγ4 H7 TCR was replaced by a Vγ2-coding sequence, the TCR activation by the BTNL3/8 expressing cells was retained.

Figures 6A, 6B:
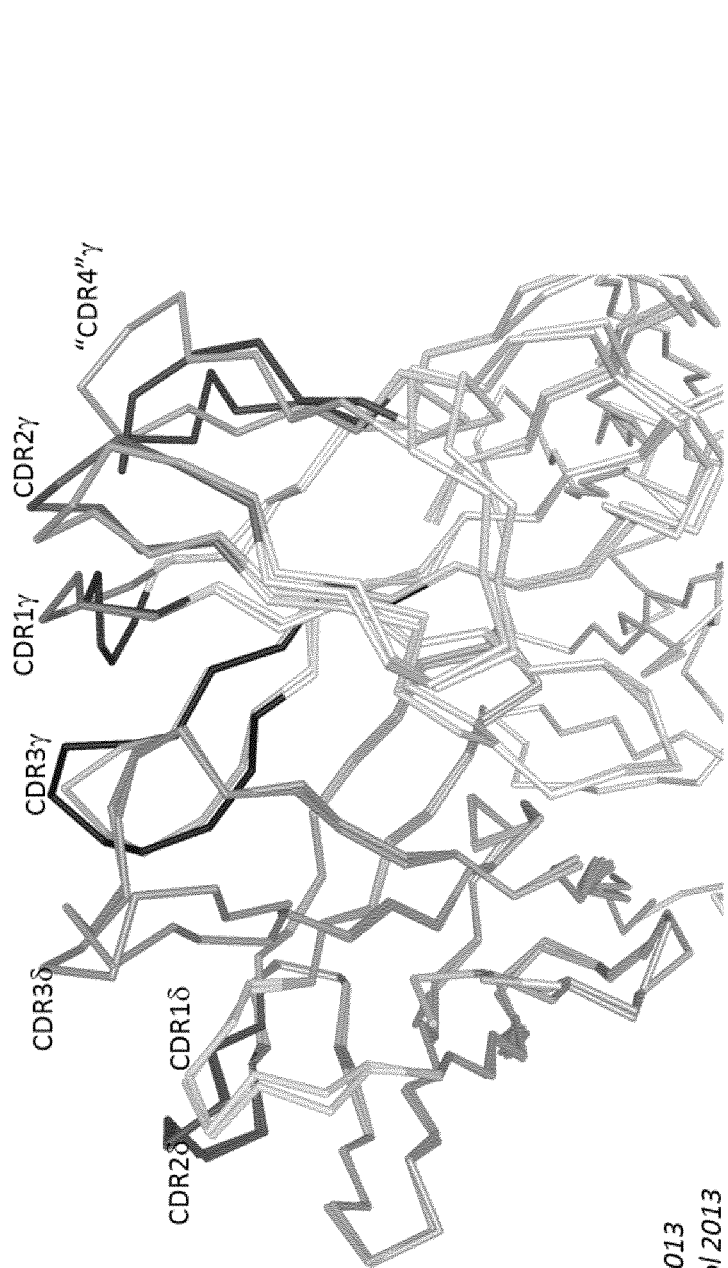

FIG. 6A shows the V domain sequence alignment of a portion of human Vγ2 and human Vγ4. CDR1, CDR2 and CDR3 are shown in shaded boxes. Nine (9) amino acids in total are different. Four differing amino acids are located in Framework Region 3, which is between CDR2 and CDR4, which we define herein as "CDR4".

FIG. 6B shows the published structures of a Vγ4/Vδ1 paired variable domains and Vγ5/Vδ1 paired variable domains aligned using Cn3D. The CDR4 region forms a proper loop indistinguishable from classical CDRs. Of note, the CDR4 loops of Vγ4 versus Vγ5 show notable conformation differences.

Figure 7:
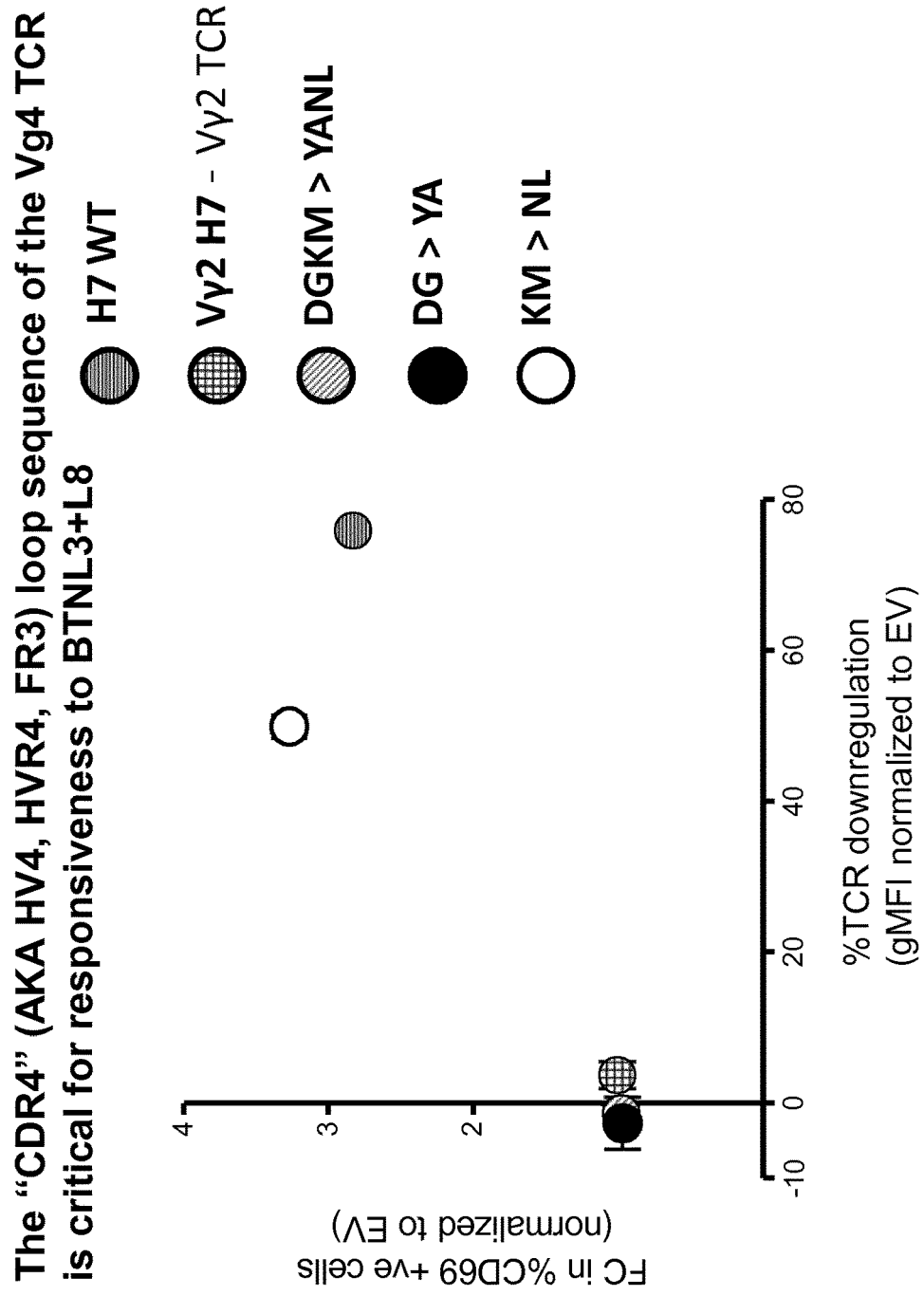

FIG. 7 shows the fold change (FC) in % CD69 expression in transduced cells (+ve cells) normalized to cells expressing empty vector (EV) and the percent TCR downregulation in J76 cells expressing Vγ4 TCR (H7 WT), Vγ2 TCR with the H7 CDR3 (Vγ2 H7), and Vγ4 TCR with amino acid substitutions within the CDR4. YA substitutions at amino acid positions 87 and 90 abrogated TCR activation by the BTNL3/8-expressing cells; whereas NL substitutions at amino acid positions 94 and 98 did not abrogate TCR activation by the BTNL3/8-expressing cells.

Figure 8:

FIG. 8 is a schematic illustration of the design of the polypeptide chains of a soluble heterodimeric γδ TCR in which the two chains heterodimerize by leucine zipper complementarity, according to an embodiment of the invention. The Vγ or, respectively, Vδ domain is fused in-frame to a TCRα or TCRβ constant region lacking the transmembrane domain, followed by a leucine zipper sequence and a histidine tag/linker. The Vγ-containing and Vδ-containing polypeptides were expressed and allowed to dimerize post-translation.

Figure 9A:
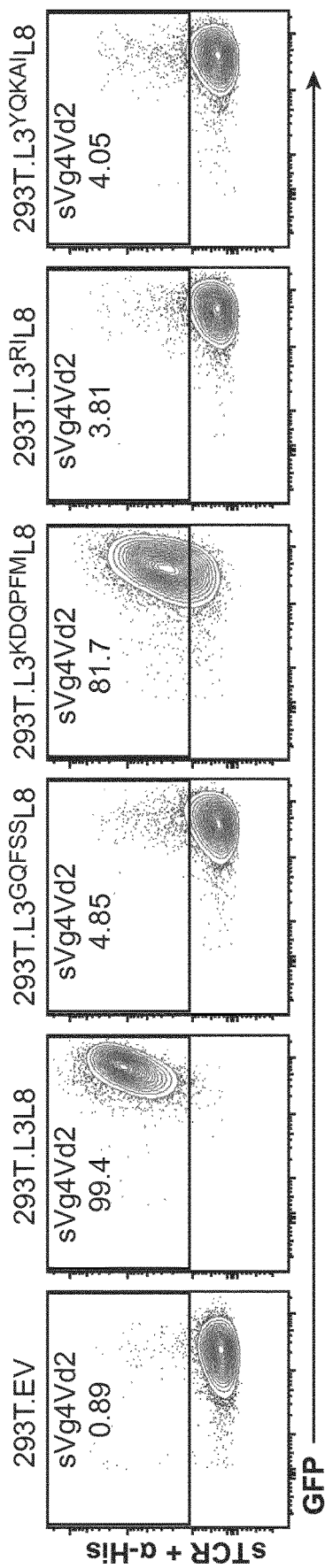

FIG. 9A shows flow cytometry results of HEK293T cells transduced with BTNL3 and BTNL8 constructs or empty vector following staining with soluble His-tagged Vγ4δ2 TCR and APC anti-His tag antibody.

Figure 9B:
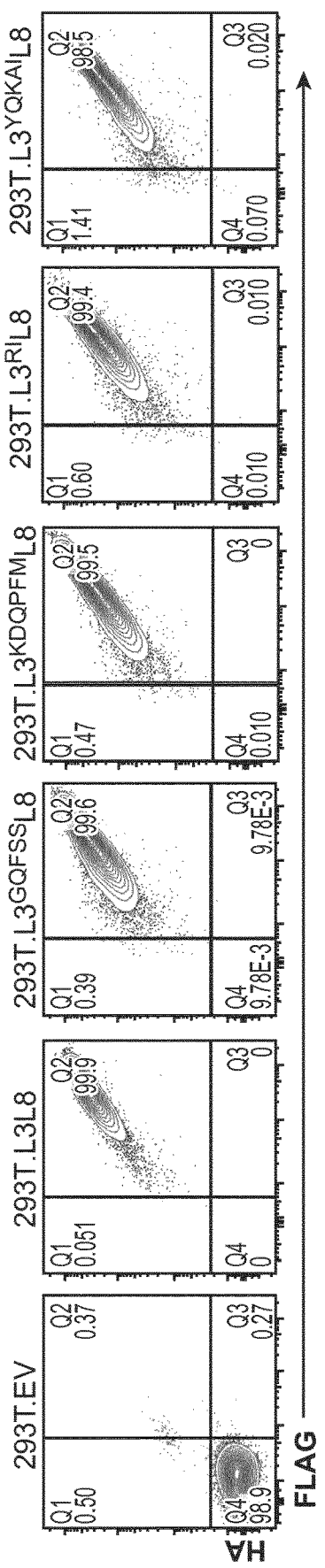

FIG. 9B shows flow cytometry results of HEK293T cells transduced with BTNL3 and BTNL8 constructs or empty vector following parallel staining with anti-FLAG and anti-HA antibodies.

Figure 10:
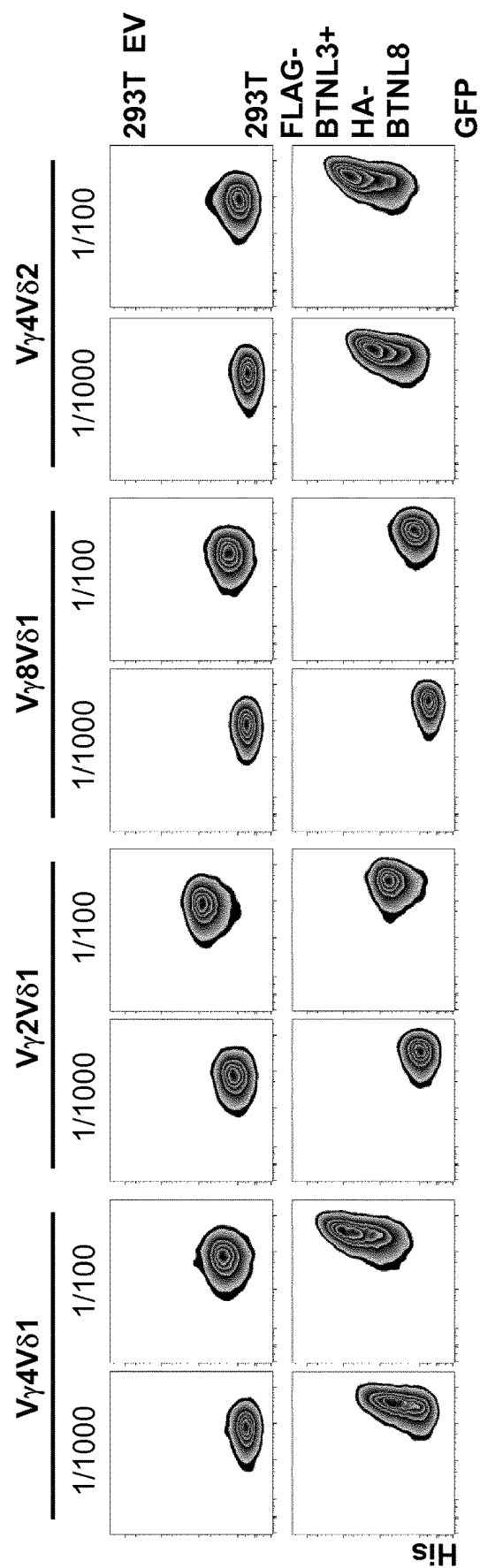

FIG. 10 shows staining with the soluble TCRs constructed as described in FIG. 8. Vγ4Vδ1 soluble TCR and Vγ4Vδ2 soluble TCR show strong binding to BTNL3+BTNL8-expressing but not empty vector (EV) control cell lines.

FIG. 11A is a schematic depicting BTNL3+BTNL8-expressing cells incubated with soluble His-tagged TCR and anti-His tag antibody at 4° C.

FIG. 11B is a schematic depicting BTNL3+BTNL8-expressing cells incubated with soluble His-tagged TCR and anti-His tag antibody at 37° C.

Figure 12:
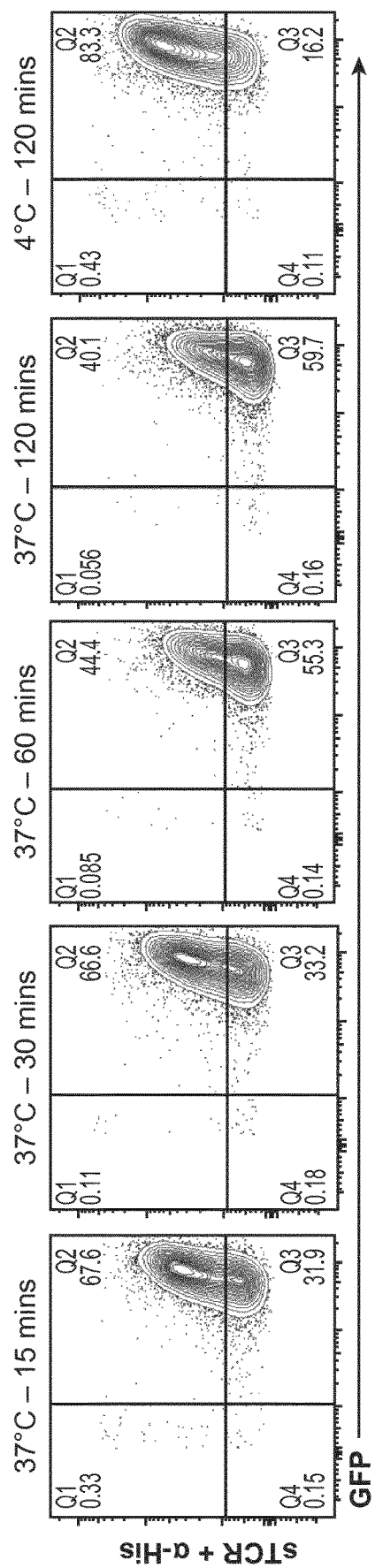

FIG. 12 is a time-course of internalization of soluble TCR at 37° C. by BTNL3+BTNL8-expressing cells.

Figure 13A:
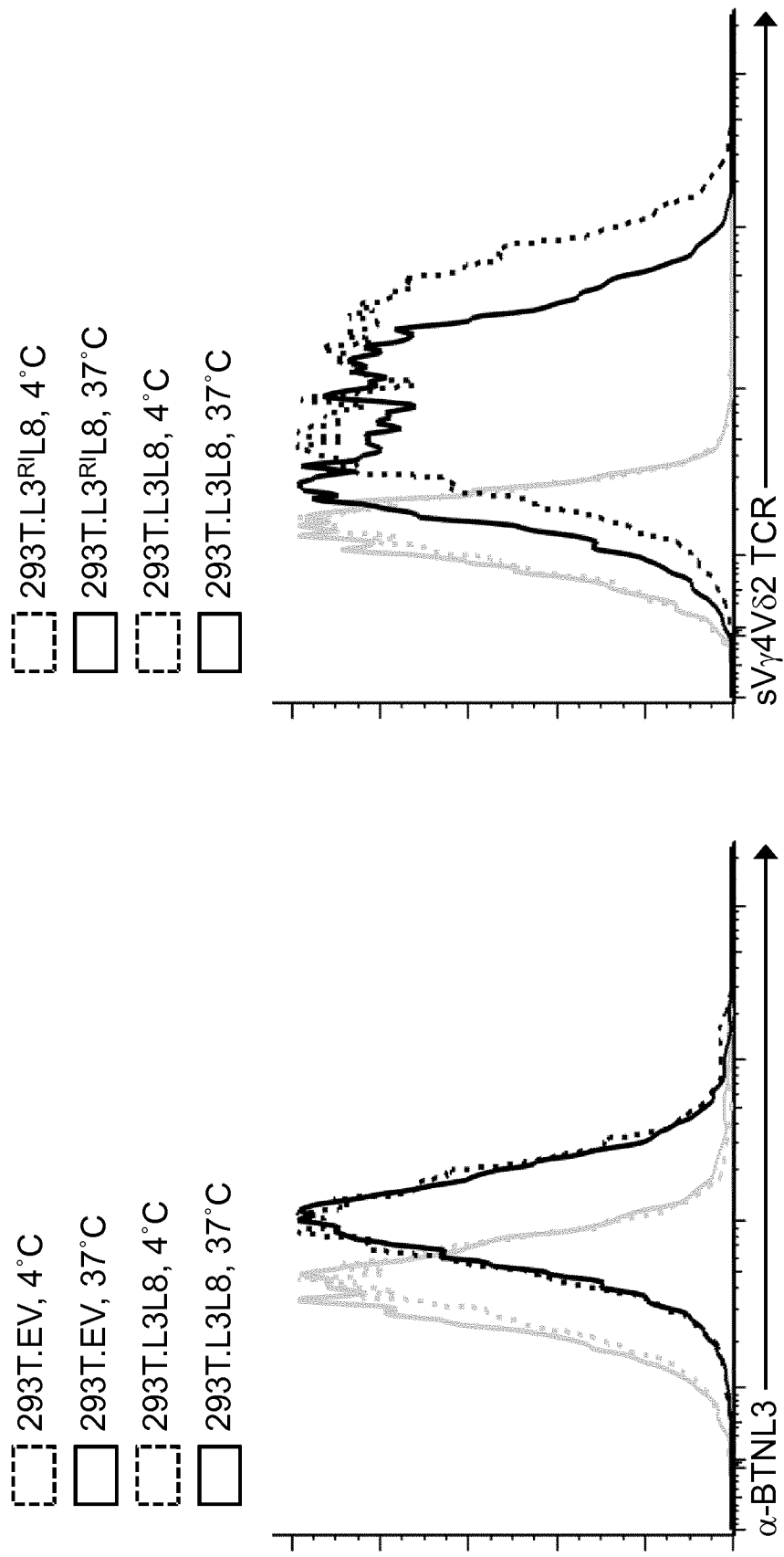

FIG. 13A shows the comparison of staining cells expressing BTNL3 and BTNL8 constructs with anti-BTNL3 antibody and soluble TCR.

Figure 13B:
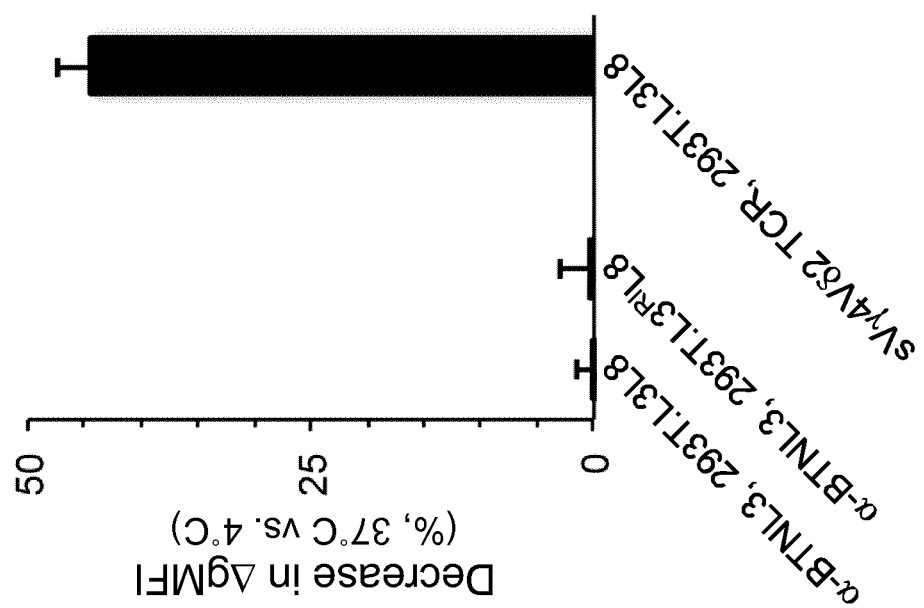

FIG. 13B shows the decrease in fluorescence of cells incubated with anti-BTNL3 antibody compared to soluble TCR.

Figure 14:
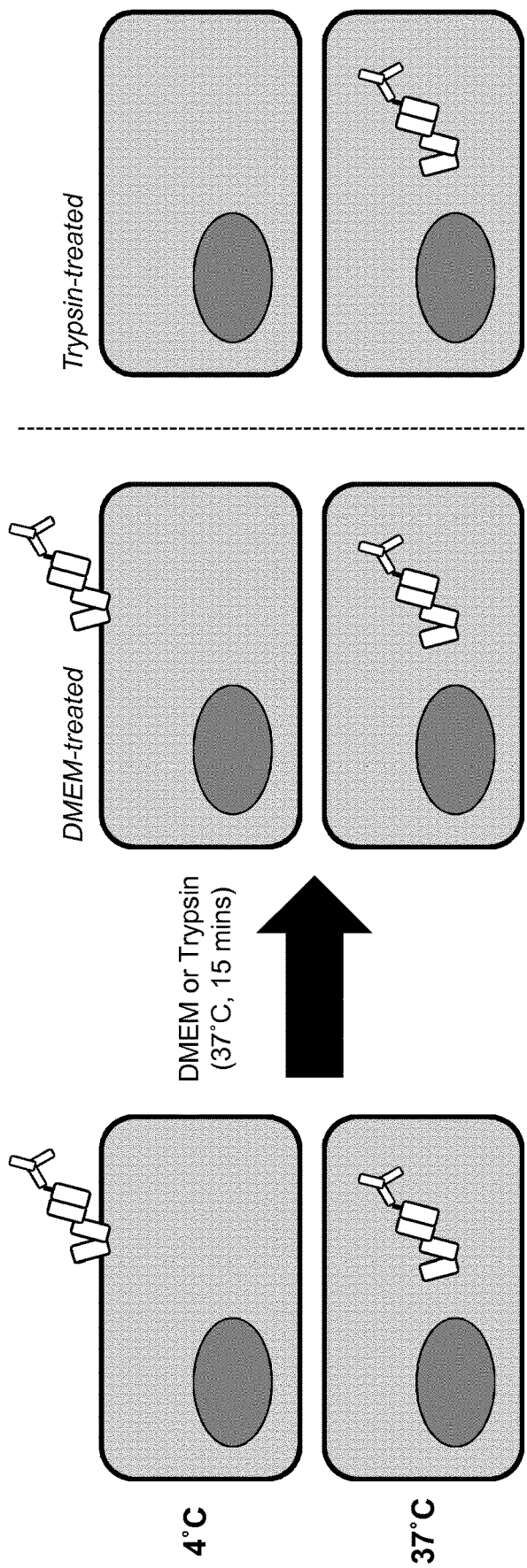

FIG. 14 is a schematic depicting the method for assessing payload delivery by soluble TCR.

Figure 15A:
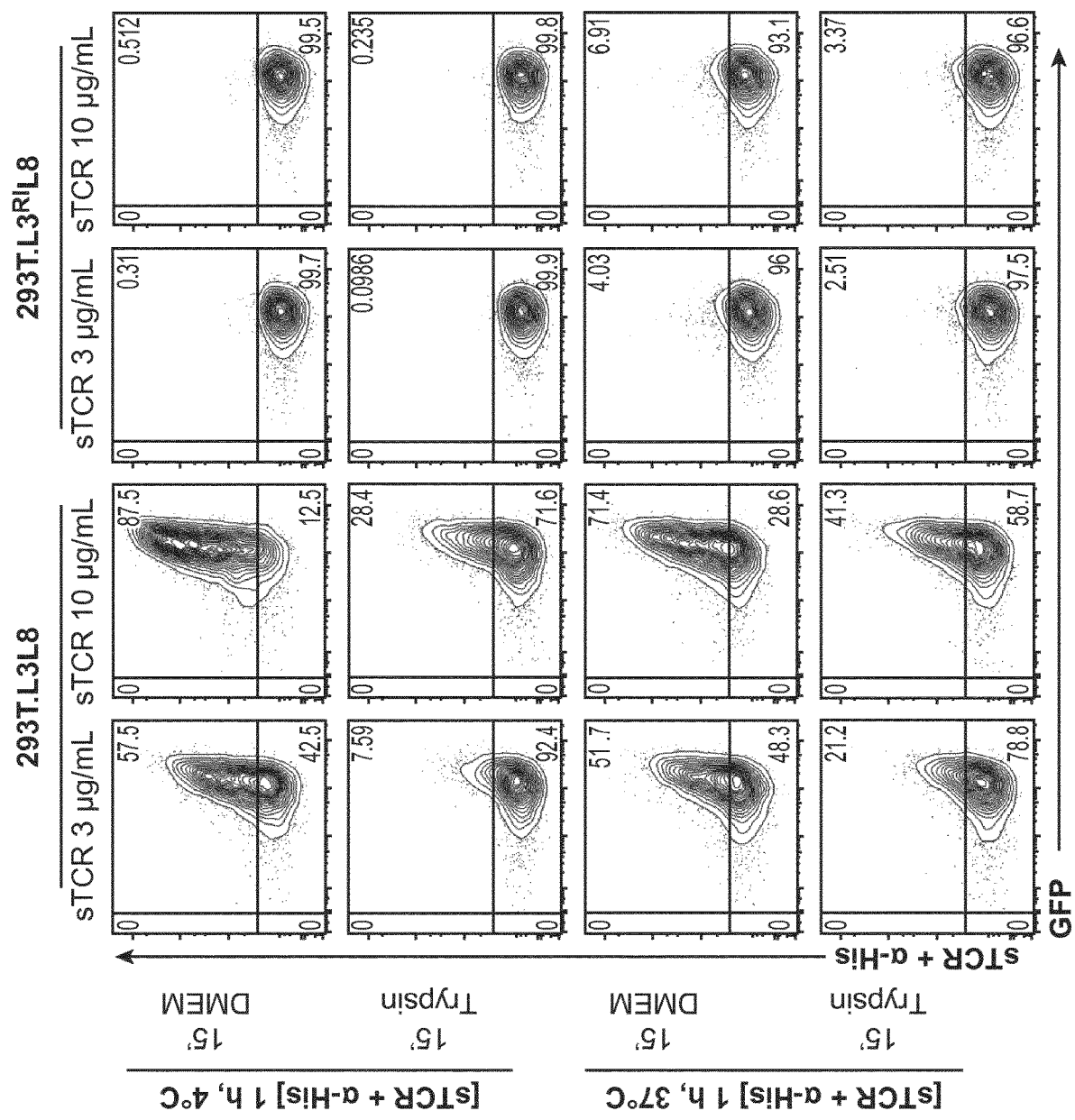
Figure 15B:
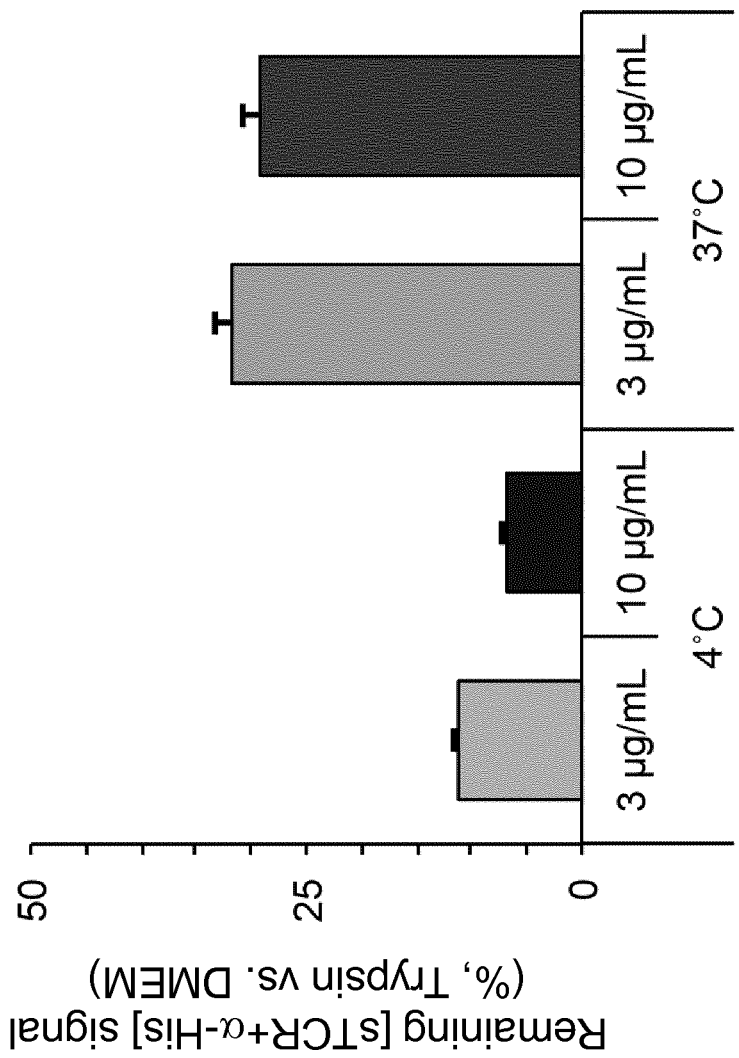

FIG. 15A shows results of an experiment assessing internalization of soluble TCR+α-His antibody complexes in cells expressing BTNL3 and BTNL8 constructs. FIG. 15B is a graph showing the remaining fluorescence signal following trypsin treatment in cells incubated with soluble TCR+α-His antibody complexes at 4° C. and 37° C.

Figure 16A:
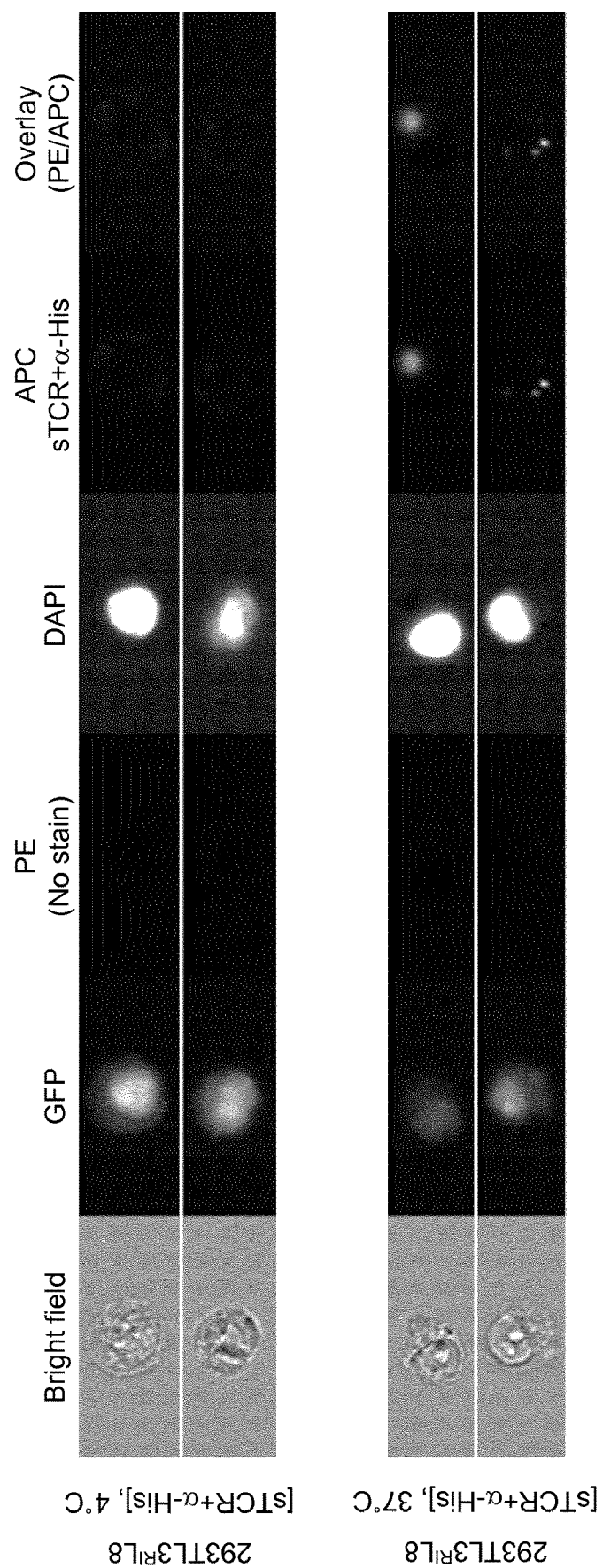

FIG. 16A shows Image Cytometry results of 293T.L3$^{R/}$L8 cells incubated with soluble TCR+α-His antibody complexes at 4° C. and 37° C. and treated with DMEM.

Figure 16B:
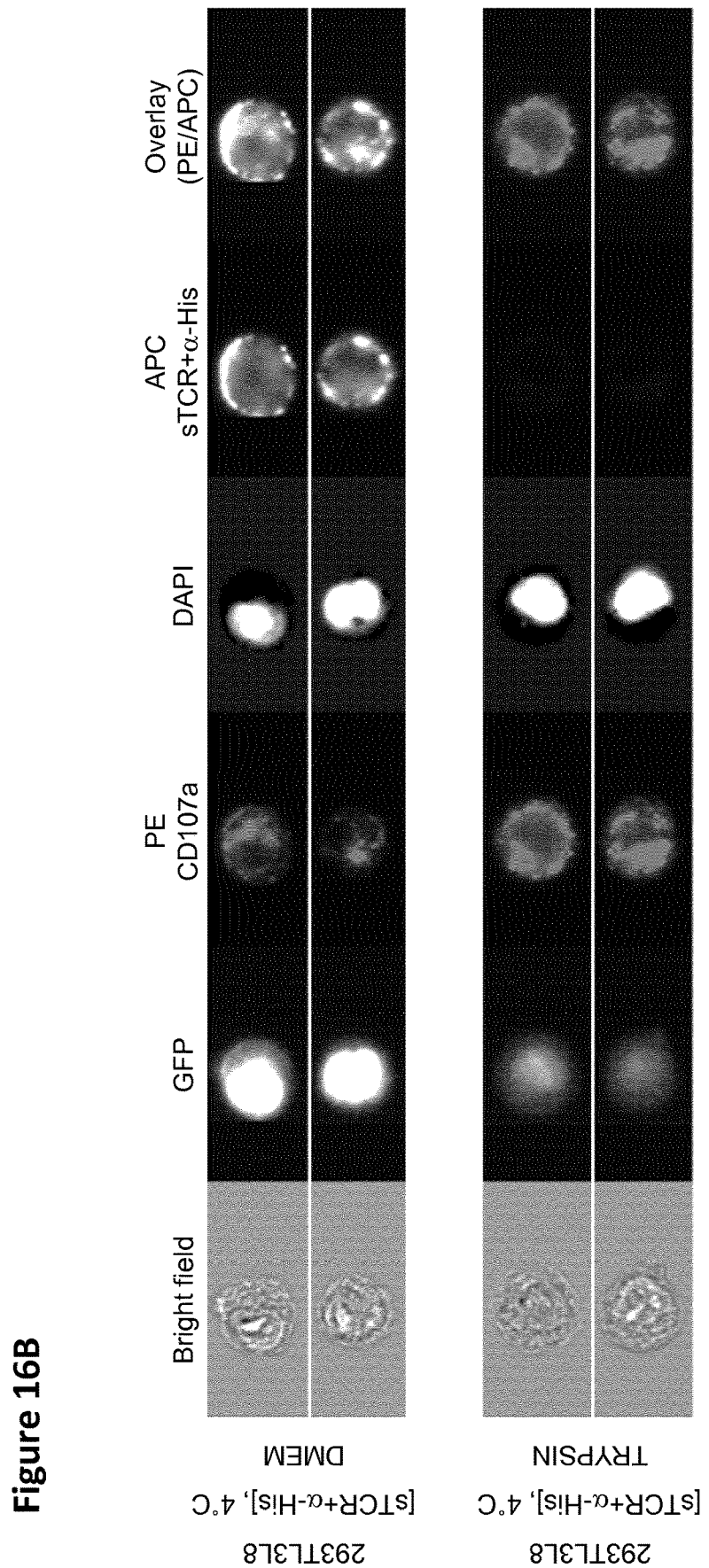

FIG. 16B shows Image Cytometry results of 293T.L3L8 cells incubated with soluble TCR+α-His antibody complexes at 4° C. and treated with DMEM or trypsin.

Figure 16C:
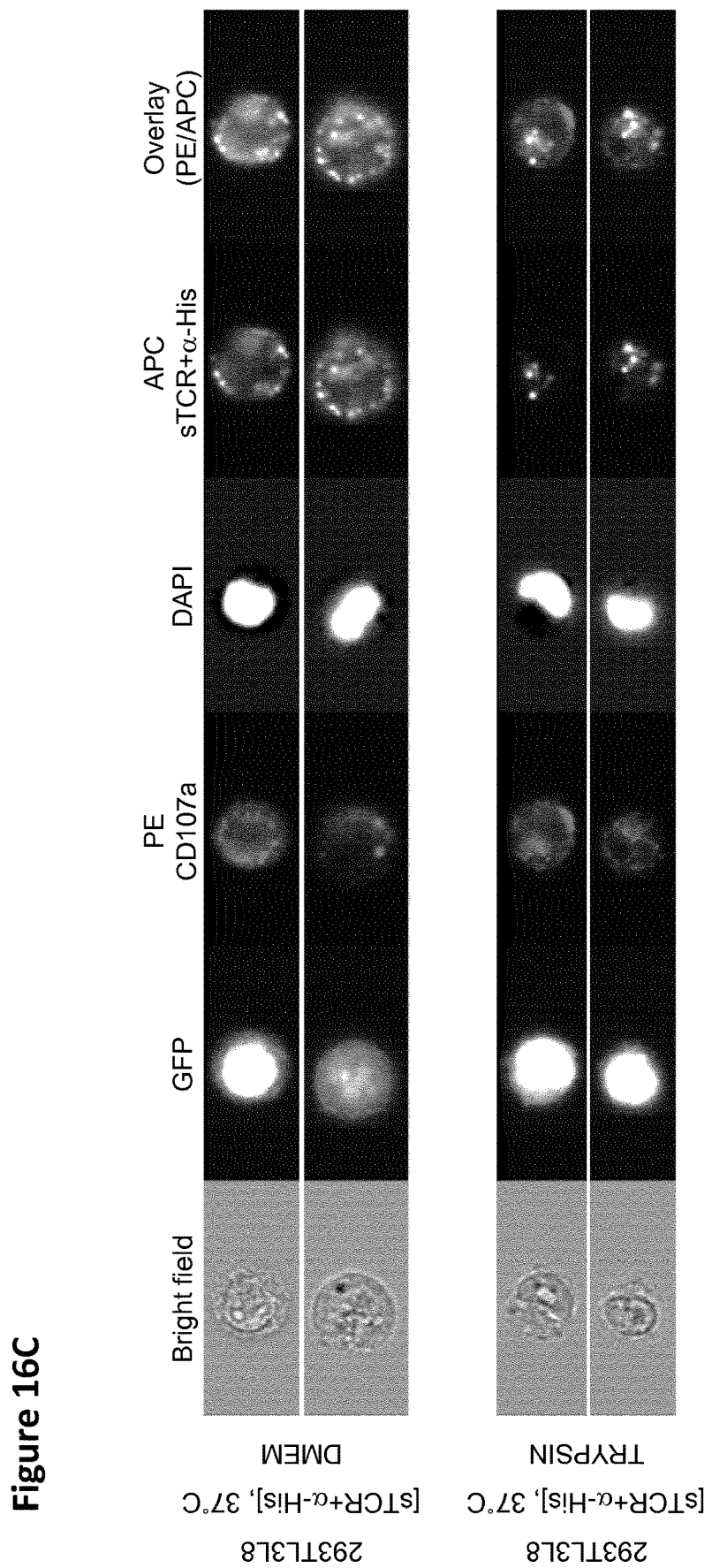

FIG. 16C shows Image Cytometry results of 293T.L3L8 cells incubated with soluble TCR+α-His antibody complexes at 37° C. and treated with DMEM or trypsin.

The figures depict various embodiments of the present invention for purposes of illustration only. One skilled in the art will readily recognize from the following discussion that alternative embodiments of the structures and methods illustrated herein may be employed without departing from the principles of the invention described herein.

6. DETAILED DESCRIPTION

6.1. Definitions

Unless defined otherwise, all technical and scientific terms used herein have the meaning commonly understood by a person skilled in the art to which this invention belongs.

As used herein, the following terms have the meanings ascribed to them below.

"Protein construct", as used herein, refers to one or more polypeptide chains that comprise at least 2 functional elements: a BTNL3/8 targeting moiety and a payload. The payload may or may not be a protein payload.

"BTNL3/8", as used herein, refers to butyrophilin protein 3 (BTNL3) and butyrophilin protein 8 (BTNL8) proteins. "BTNL3/8" may refer to BTNL3 without BTNL8, BTNL8 without BTNL3, or BTNL3 and BTNL8 heterodimers.

"BTNL 3/8 Targeting moiety", as used herein, refers to a molecule that specifically binds BTNL3/8." In certain embodiments, the BTNL3/8 targeting moiety is an antigen binding protein. In certain embodiments, the BTNL3/8 targeting moiety is at least a portion of a Vγ domain polypeptide.

"Vγ domain", as used herein, refers to the variable domain of a T cell receptor (TCR) gamma chain. The Vγ domain includes the J region and complementarity-determining regions (CDR) CDR1, CDR2, CDR3 and CDR4. Vγ domain residue numbering is as shown in FIG. 1, in which residue 19 is the N-terminal amino acid of the mature Vγ domain after cleavage of the signal sequence. For a Vγ domain not shown in FIG. 1, residue numbering is assigned after best alignment to the sequences in FIG. 1. A "corresponding residue" of a Vγ domain is an amino acid at the same numbered position as the residue to which it is said to correspond.

"Vγ domain CDR4", as used herein, refers to a 16 consecutive amino acid portion of a Vγ domain located between the CDR2 and CDR3 regions, corresponding to amino acid sequence positions 85-100 of FIG. 1. The amino acid sequence of CDR4 of the human Vγ4 domain has the sequence of SEQ ID NO: 3. The amino acid sequence of CDR4 of the human δγ2 domain is SEQ ID NO. 5. The amino acid sequence of CDR4 of the mouse Vγ7 domain is SEQ ID NO: 4.

"Payload", as used herein, refers to any molecule that is delivered to target cells of interest (e.g., cells expressing BTNL3/8 and/or intestinal epithelial cells). The payload may comprise nucleotides, nucleotides (e.g., nucleotides comprising a detectable moiety or a toxin or that disrupt transcription), nucleic acids such as DNA and RNA (e.g., mRNA, RNAi, miRNA, siRNA, snRNA, snoRNA, piRNA, exRNA, scaRNA and lncRNA), amino acids (e.g., amino acids comprising a detectable moiety or a toxin or that disrupt translation), polypeptides (e.g., enzymes, biologics), lipids, carbohydrates, small molecules (e.g., small molecule drugs and toxins) and combinations thereof. In certain embodiments, the payload is a therapeutic agent. Therapeutic agents include, but are not limited to, chemotherapeutic agents, imaging agents (e.g., radioisotopes), immunomodulators (e.g., cytokines, chemokines, or checkpoint inhibitors), and toxins (e.g., cytotoxic agents). In certain embodiments, the payload is an antibody.

"Linker", as used herein, refers to any molecule that can be used to join functional elements of the protein construct (e.g., a targeting moiety and a payload). In certain embodiments, the linker can used to allow site-specific conjugation of a molecule to a functional element (e.g., a targeting moiety or a payload) of the protein construct. In certain embodiments, the linker may be used to identify or detect the protein construct in vitro or in vivo.

"Peptide Linker", as used herein, refers to a linker that is a polypeptide. In certain embodiments, the peptide linker is fused, in-frame to functional elements of the protein construct (e.g., a targeting moiety and a payload). In certain embodiments the peptide linker allows site-specific conjugation of a molecule to an element of the protein construct. A peptide linker may be of any length and of any amino acid sequence that permits the desired conformation of the functional elements to which the peptide linker is fused.

"Internal linker", as used herein, refers to a polypeptide sequence that is covalently bound to at least one additional polypeptide on both its N-terminus and C-terminus. In certain embodiments, the internal linker is a polypeptide chain within the targeting moiety (e.g., an internal linker between a Vγ and Vδ domain). An internal linker may be of any length and of any amino acid sequence that permits the desired conformation of the additional polypeptides to which the internal linker is fused.

"Antibody", as used herein, includes any antibody protein construct comprising at least one antibody variable domain comprising at least one antigen binding site (ABS). Antibodies include, but are not limited to, variable domain only molecules, single chain variable fragments (scFv), single chain Fab fragments (scFab), bispecific antibodies, hybrid IgGs, Fab fusion proteins, Fc-modified IgGs, appended IgGs, Diabodies, scDiabodies, DARTs, tandAbs and minibodies.

"Single chain in-frame fusion", as used herein, refers to single chain in-frame fusion T cell receptor variable domains (scTv) wherein at least a portion of at least two polypeptide variable domains of a T-Cell receptor that are produced as a single fused polypeptide chain wherein the variable domains sequences are fused in-frame. Single chain in-frame fusion T cell receptor variable domains (scTv) may comprise more than one variable domain and/or constant region and may be paired with a T cell receptor of any origin. As such, scTvs include tandem scTvs wherein 2 or more variable domains are fused in frame.

"Antigen binding site" (ABS), as used herein, as used herein, refers to a region of an antibody molecule that specifically recognizes or binds to a given antigen or epitope. The ABS is said to bind to its specific antigen or epitope with a particular affinity. As described herein, "affinity" refers to the strength of interaction of non-covalent intermolecular forces between one molecule and another. The affinity, i.e., the strength of the interaction, can be expressed as a dissociation equilibrium constant ($K_D$), wherein a lower $K_D$ value refers to a stronger interaction between molecules. $K_D$ values of antibody constructs are measured by methods well known in the art including, but not limited to, bio-layer interferometry (e.g., Octet/FORTEBIO®), surface plasmon resonance (SPR) technology (e.g., Biacore®), and cell binding assays. The affinity between an ABS and its cognate antigen or epitope has a $K_D$ value below $10^{-6}$M, $10^{-7}$M, $10^{-8}$M, $10^{-9}$M, or $10^{-10}$M.

"Small molecule", as used herein, refers to a molecule having a low molecular weight of less than <900 daltons and does not include peptides. Small molecules include organic molecules that may regulate a biological process, having a size in the order of 1 nm.

"Anti-inflammatory cytokine", as used herein, refers to any cytokine with anti-inflammatory activity. Anti-inflammatory cytokines include, but are not limited to: Interleukin (IL) IL-1ra, IL-4, IL-6, IL-10, IL-11, IL-13, and Transforming growth factor R (TGFβ).

"Anti-proinflammatory agent", as used herein, refers to any molecule or agent that inhibits the activity or expression of a pro-inflammatory cytokine. Anti-proinflammatory agents comprise inhibitors of pro-inflammatory cytokines which include, but are not limited to, interleukin-1 (IL-1), IL-12, IL-18, Tumor Necrosis Factor Alpha (TNFα), interferon gamma (INF-γ) and granulocyte-macrophage colony stimulating factor. Anti-proinflammatory agents include soluble cytokine receptors with anti-inflammatory activities such as, soluble Tumor Necrosis Factor receptor p55, Soluble Tumor Necrosis Factor, p75, Soluble IL-1 receptor type 2, IL-18 binding protein. Anti-proinflammatory agents also includes cytokine receptors that lack intracellular signaling that compete with pro-inflammatory cytokine receptors such as, membrane-bound IL-1 receptor type 2.

"Immunomodulator", as used herein, refers to any molecule that changes an immune response and/or activity of a cell of the immune system. In certain embodiments, an immunomodulator is an immune suppressor or an immune stimulator. "Immune suppressors" refers to any molecule or agent that reduces an immune response and/or activity of a cell of the immune system, whereas "immune suppressors" refers to any molecule or agent that increases an immune response and/or activity of a cell of the immune system.

"Immune-related condition", as used herein, refers to any condition or disorder associated with altered activity of the immune system. Immune-related conditions include conditions associated with an increased or decreased immune response. Immune-related conditions include, but are not limited to: autoimmune diseases, inflammatory conditions, allergic reactions, immunodeficiency, hematopoietic cancers and other hematopoietic abnormalities.

"Inflammatory condition", as used herein, refers to any condition or disorder associated with increased inflammation or presence of inflamed tissue(s). Inflammatory conditions include, but are not limited to: asthma, atherosclerosis, autoimmune diseases, autoinflammatory diseases, cancer, celiac disease, chronic prostatitis, colitis, diverticulitis, glomerulonephritis, hidradenitis suppurativa, hypersensitivities, inflammatory bowel disease, interstitial cystitis, lichen planus, mast cell activation syndrome, mastocytosis, otitis, pelvic inflammatory disease, reperfusion injury, rheumatic fever, rheumatoid arthritis, rhinitis, sarcoidosis, transplant rejection and vasculitis.

"Condition of the gastrointestinal system", as used herein, refers to any condition or disorder associated with any tissues of the gastrointestinal system. Conditions of the gastrointestinal system, include, but are not limited to, immune-related conditions of the gastrointestinal system, inflammatory conditions of the gastrointestinal system, microbial infection of tissues of the gastrointestinal system and conditions caused by dietary abnormalities, metabolic disorders or deficiencies. Conditions of the gastrointestinal system include, but are not limited to, inflammatory bowel disease, celiac disease, irritable bowel syndrome, diverticulitis, Crohn's disease, and cancer (e.g., colon cancer, rectal cancer, stomach cancer).

As used herein, the terms "treat" or "treatment" refer to both therapeutic treatment and prophylactic or preventative measures, wherein the object is to prevent or slow down (lessen) an undesired physiological change or disorder, such as the progression of multiple sclerosis, arthritis, or cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal", is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, and so on.

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease. A therapeutically effective amount can be a "prophylactically effective amount" as prophylaxis can be considered therapy.

The term 'recombinant human γδ TCR protein' or derivatives of this term as referred to throughout this document relate to any recombinant protein generated from human γδ TCR sequence or functional derivatives or homologues thereof by standard genetic engineering methodologies. Such recombinant proteins may also include additional fusion elements such as dimerization domains. Non-limiting examples include fusions to support correct folding of the TCR, fusions to operate as transmembrane domains (e.g., to support correct presentation of the TCR on the surface of a cell membrane), or fusions to extend half-life or increase size (e.g., human serum albumin fusion domains) or payload fusions as described elsewhere herein. These additional fusion elements can be generated with sequences derived from γδ TCR sequence or derivatives and homologues thereof, or alternatively such fusion sequences can be non-TCR in origin.

The term 'recombinant γδ TCR sequences' or 'recombinant human TCR libraries' or 'recombinant human TCR panel' or derivative terms therefrom as referred to throughout this document relate to a collection of more than one recombinant human γδ TCR proteins, or more than two, or three, or four, or five, or more than ten recombinant human γδ TCR proteins. This collection will comprise a collection of sequences differing by at least one amino acid or more. This collection of recombinant TCRs can be presented in a soluble form. Alternatively, for display purposes this collection can also be linked or fused or tethered to inorganic or organic materials (non-limiting examples include 'beads' or 'plates' or 'columns' or 'phages'). Alternatively, such a collection can also be presented or displayed on a membrane or collection of membranes such as those found in intact or living cells or non-living membranes such micelles. When expressing and presenting such a collection on a living cell or cells it is typical to also generate a collection of cognate expression vectors. This collection of cognate expression vectors can be used to first engineer the cell or cells to display said recombinant human γδ TCR proteins or library or panel or collection of said proteins to create libraries of cells expressing such TCR proteins.

The term 'cognate binding partner' or 'candidate cognate binding partners' or derivative terms therefrom as referred to throughout this document relate to proteins or derivatives therefrom identified as binding recombinant human γδ TCR proteins in a sequence specific manner. For discovery or screening or validation of such cognate binding partners, they can be presented or displayed in their natural context (e.g. on the surface of a cell or cells). They can also be presented or displayed as extracts or secretions from such cells, purified derivatives therefrom, or in recombinant form.

6.2. Other Interpretational Conventions

Unless otherwise specified, all references to sequences herein are to amino acid sequences.

In this disclosure, "comprises," "comprising," "containing," "having," "includes," "including," and linguistic variants thereof have the meaning ascribed to them in U.S. patent law, permitting the presence of additional components beyond those explicitly recited.

Ranges provided herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless specifically stated or apparent from context, as used herein the term "or" is understood to be inclusive. Unless specifically stated or apparent from context, as used herein, the terms "a", "an", and "the" are understood to be singular or plural.

Unless specifically stated or otherwise apparent from context, as used herein the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

6.3. Protein Constructs Comprising a BTNL3/8 Targeting Moiety

In a first aspect, protein constructs are provided. The protein constructs comprise a BTNL3/8 targeting moiety, a payload, and an optional linker linking the targeting moiety to the payload.

6.3.1.1 BTNL3/8 Targeting Moiety

The BTNL3/8 targeting moiety specifically binds to human BTNL3, human BTNL8 and/or human BTNL3/8 heterodimer. In certain embodiments, the BTNL3/8 targeting moiety is at least a portion of a T cell receptor (TCR) Vγ domain polypeptide, as described in further detail below. In alternative embodiments, the BTNL3/8 targeting moiety is an antigen binding site of an antibody. In certain embodiments, the BTNL3/8 targeting moiety inhibits or partially inhibits BTNL3/8 function upon binding of the BTNL3/8 targeting moiety to the BTNL3/8. In certain embodiments, the BTNL3/8 targeting moiety stimulates or activates the BTNL3/8 function upon binding of the BTNL3/8 targeting moiety to the BTNL3/8. In certain embodiments, the BTNL3/8 targeting moiety inhibits or partially inhibits BTNL3/8 heterodimer function upon binding of the BTNL3/8 targeting moiety to the BTNL3/8 heterodimer. In certain embodiments, the BTNL3/8 targeting moiety stimulates or activates the BTNL3/8 heterodimer function upon binding of the BTNL3/8 targeting moiety to the BTNL3/8 heterodimer.

6.3.1. TCR Gamma Variable Domain

In certain embodiments, the BTNL3/8 targeting moiety comprises at least a portion of a T cell receptor (TCR) Vγ domain polypeptide. In typical embodiments, the BTNL3/8 targeting moiety comprises a Vγ domain polypeptide.

In certain embodiments, the BTNL3/8 targeting moiety comprises CDR4 region derived from Vγ4. In certain embodiments, the BTNL3/8 targeting moiety comprises a Vγ domain wherein the amino acid at sequence position number 87 of the Vγ domain is aspartic acid or histidine, and the amino acid at sequence position number 90 of the Vγ domain is glycine or glutamic acid, and wherein the remaining residues of the Vγ CDR4 are, at each position, independently selected from the corresponding residues of a human or murine Vγ domain.

In certain embodiments, the remaining residues of the Vγ domain CDR4 are, at each position, independently selected from the corresponding residues of human Vγ4, human Vγ2, or mouse Vγ7. In some embodiments, the remaining residues of the Vγ domain CDR4 are all selected from the corresponding residues of human Vγ4, human Vγ2, or mouse Vγ7. In an embodiment, the remaining residues of the Vγ CDR4 are all selected from the corresponding residues of human Vγ4. In an embodiment, the remaining residues of the Vγ CDR4 are all selected from the corresponding residues of human Vγ2. In an embodiment, the remaining residues of the Vγ CDR4 are all selected from the corresponding residues of mouse Vγ7. In an embodiment, the amino acid sequence at positions numbers 87-90 of the Vγ domain is SEQ ID NO: 1. In an embodiment, the amino acid sequence at positions numbers 87-90 of the Vγ domain is SEQ ID NO: 2.

In certain embodiments, the Vγ domain is a Vγ domain sequence shown in FIG. 1. In certain embodiments, the Vγ domain is a human Vγ domain. In an embodiment, the Vγ domain is a human Vγ4 domain. In an embodiment, the Vγ domain is a human Vγ2 domain in which the amino acids of the CDR4 are substituted with aspartic acid or histidine at amino acid sequence position number 87 and substituted with glycine or glutamic acid at amino acid sequence position number 90.

In certain embodiments, the Vγ domain is human Vγ3 or human Vγ5. In particular embodiments, the Vγ domain is human Vγ3 or human Vγ5 in which the amino acids of the CDR4 are substituted with aspartic acid or histidine at amino acid sequence position number 87 and substituted with glycine or glutamic acid at amino acid sequence position number 90. In certain embodiments, the Vγ domain is a human Vγ domain that has at least 70% sequence identity to human Vγ4.

In certain embodiments, the Vγ domain is Vγ domain that is non-human mammal Vγ domain. In certain embodiments, the Vγ domain is a non-human mammalian Vγ domain sequence that has at least 70% identity to human Vγ4.

In some embodiments, the Vγ domain CDR3 is a human or mouse Vγ CDR3 sequence. In certain embodiments, the Vγ domain CDR3 comprises a human CDR3 sequence. In particular embodiments, the Vγ domain CDR3 comprises a human Vγ4 CDR3 sequence. In particular embodiments, the Vγ domain CDR3 comprises a human Vγ2 CDR3 sequence. In certain embodiments, the Vγ domain CDR3 comprises a non-human mammalian CDR3 sequence. In an embodiment, the Vγ domain CDR3 comprises a mouse Vγ7 CDR3 sequence.

In some embodiments, the J region is a Vγ J region. In certain embodiments, the J region is a human Vγ J region. In certain embodiments, the J region is a mouse Vγ J region.

In an embodiment, the J region has a polypeptide sequence selected from the group consisting of SEQ ID NOs:15-18.

6.3.1.1.1 Paired with Vδ

In certain embodiments, the BTNL3/8 targeting moiety of the protein construct further does not comprise a paired Vδ domain. In certain embodiments, the BTNL3/8 targeting moiety of the protein construct comprises a Vγ domain paired with at least an additional Vγ domain. In certain embodiments, the BTNL3/8 targeting moiety is a Vγ4 homodimer. In certain embodiments, the BTNL3/8 targeting moiety of the protein construct further comprises a paired Vδ domain. In certain embodiments, the Vδ domain is a human Vδ domain. In certain embodiments, the human Vδ domain is Vδ1, Vδ2, Vδ3, Vδ5 or Vδ8. In an embodiment, the human Vδ domain is Vδ1. In certain embodiments, the Vδ domain is a non-human mammalian Vδ domain.

(a) Heterodimer Format

In some embodiments, the Vδ domain is paired by heterodimerization of a first and second polypeptide, one of which comprises a Vγ domain, one of which comprises a Vδ domain.

The heterodimeric interaction can include covalent and/or non-covalent interactions between polypeptides comprising a Vγ domain and a Vδ domain. In typical embodiments, the Vγ domain and the Vδ domain are paired by orthogonal features in which homodimers form less well than heterodimers.

In some embodiments, the polypeptides respectively comprising the Vγ domain and the Vδ domain are covalently linked by at least one engineered disulfide bridge. Engineered disulfide bridges are amino acid sequences that provide non-endogenous cysteine amino acids in two or more domains such that a non-native disulfide bond forms when the two or more domains associate. In certain of these embodiments, at least one disulfide bridge is engineered within the Vγ and Vδ domains. In certain embodiments, at least one disulfide bridge is engineered in a domain outside the variable regions, such as within constant regions fused in frame with the variable regions.

In some embodiments, the heterodimeric interaction is leucine zipper complementarity.

In certain embodiments, one or more of the polypeptides of the paired Vγ/Vδ heterodimer further comprises a T cell receptor constant region. In certain embodiments, a first T cell receptor constant region is fused in-frame to the C terminus of the paired Vγ domain. In an embodiment, the first T cell receptor constant region is a human TCR constant region. In an embodiment, the first T cell receptor constant region is a human TCR β constant region. In an embodiment, the first T cell receptor constant region is a human TCR α constant region. In an embodiment, the first T cell receptor constant region is a human TCR γ constant region. In an embodiment, a polypeptide of the paired Vγ/Vδ heterodimer further comprises a second T cell receptor constant region, wherein the second T cell receptor constant region is fused in-frame to the C terminus of the paired Vδ domain. In an embodiment, the second T cell receptor constant region is a human TCR α constant region. In an embodiment, the second T cell receptor constant region is a human TCR β constant region. In an embodiment, the second T cell receptor constant region is a human TCR δ constant region.

In some embodiments, the in-frame fusion of the Vγ domain with a first constant region comprises an internal linker sequence between the Vγ domain and the first TCR constant region. In some embodiments, the in-frame fusion of the Vδ domain and the second TCR constant region comprises an internal linker sequence between the Vδ domain and the second T cell receptor constant region.

In an embodiment, the BTNL3/8 targeting moiety comprises SEQ ID NO: 9. In an embodiment, the BTNL3/8 targeting moiety comprises SEQ ID NO: 10. In an embodiment, the BTNL3/8 targeting moiety comprises SEQ ID NO: 11.

In certain embodiments, the BTNL3/8 targeting moiety comprises more than one Vγ domain and/or Vδ domain. In certain embodiments, the more than one Vγ domain and/or Vδ domain are multimerized. In certain embodiments, all or a portion of the more than one Vγ domain and/or Vδ domains are fused in frame to a T cell receptor constant region. In certain embodiments, the more than one Vγ domain and/or Vδ domain that are multimerized comprise one or more internal linkers.

In a further aspect, recombinant γδ TCR constructs are provided. Therefore, according to a further aspect, there is provided a recombinant γδ TCR protein comprising SEQ ID NO: 9 (optionally without the C-terminal His-tag). In another aspect, there is provided a recombinant γδ TCR protein comprising SEQ ID NO: 10. In another aspect, there is provided a recombinant γδ TCR protein comprising SEQ ID NO: 11 (optionally without the C-terminal His-tag). In another aspect, there is provided a recombinant γδ TCR protein comprising SEQ ID NO: 12. In another aspect, there is provided a recombinant γδ TCR protein comprising SEQ ID NO: 13.

(b) Single Chain in Frame Fusions

In certain embodiments, the BTNL3/8 targeting moiety comprises a single chain in-frame fusion of the Vγ domain and the paired Vδ domain. In some embodiments, the Vγ domain is N terminal to the Vδ domain. In some embodiments, the Vγ domain is C terminal to the Vδ domain. In various embodiments, the single chain in-frame fusion of the Vγ domain and the Vδ domain comprises an internal linker sequence.

In some embodiments, the Vδ domain is a human Vδ domain. In an embodiment, the human Vδ domain is Vδ1, Vδ2 or Vδ5. In an embodiment, the human Vδ domain is Vδ1. In certain embodiments, the single chain in-frame fusion further comprises at least a T cell receptor constant region. In certain embodiments, the single chain in-frame fusion further comprises a first T cell receptor constant region, wherein the first T cell receptor constant region is fused in-frame to the C terminus of the Vγ domain. In an embodiment, the first T cell receptor constant region is a human T cell receptor constant region. In an embodiment, the first T cell receptor constant region is a human T cell receptor β constant region. In an embodiment, the first T cell receptor constant region is a human T cell receptor α constant region. In an embodiment, the first T cell receptor constant region is a human T cell receptor γ constant region. In an embodiment, the single chain in-frame fusion further comprises a second T cell receptor constant region wherein the second T cell receptor constant region is fused in-frame to the C terminus of the paired Vδ domain. In an embodiment, the second T cell receptor constant region is a human T cell receptor α constant region. In an embodiment, the second T cell receptor constant region is a human T cell receptor β constant region. In an embodiment, the second T cell receptor constant region is a human T cell receptor δ constant region. In an embodiment, the in-frame fusion of the Vδ domain and the second T cell receptor constant region comprises an internal linker sequence between the Vδ domain and the second T cell receptor constant region.

In certain embodiments, the single chain in-frame fusion comprises more than one Vγ domain and/or Vδ domain. In certain embodiments, the more than one Vγ domain and/or Vδ domain are multimerized. In certain embodiments, the more than one Vγ domain and/or Vδ domain that are multimerized comprise one or more internal linkers. In certain embodiments, all or a portion of the more than one Vγ domain and/or Vδ domains are fused in frame to at least a T cell receptor constant region.

6.3.2. Antibody-Based Targeting Moieties

In certain embodiments, the BTNL3/8 targeting moiety comprises an antibody that specifically binds to human BTNL3, human BTNL8 and/or human BTNL3/8 heterodimer. In certain embodiments, the antibody is a full-length antibody fragment or antibody format including, but not limited to, Fab fragments, Fvs, scFvs, tandem scFvs, Diabodies, scDiabodies, DARTs, tandAbs, minibodies, camelid VHH, and other antibody fragments or formats known to those skilled in the art. Exemplary antibody and antibody fragment formats are described in detail in Brinkmann et al., *MABS*, 2017, Vol. 9, No. 2, 182-212, herein incorporated by reference for all that it teaches.

In an embodiment, the antibody comprises an Fc domain capable of interaction with Fc receptors. In an embodiment, the antibody comprises an Fc domain incapable of interaction with Fc receptors. In certain embodiments, the antibody has one or more engineered mutations in an amino acid sequence of an antibody domain that reduce the effector functions naturally associated with antibody binding. Effector functions include, but are not limited to, cellular functions that result from an Fc receptor binding to an Fc portion of an antibody, such as antibody-dependent cellular cytotoxicity (ADCC, also referred to as antibody-dependent cell-mediated cytotoxicity), complement fixation (e.g. C1q binding), antibody dependent cellular-mediated phagocytosis (ADCP), and opsonization. Engineered mutations that reduce the effector functions are described in more detail in U.S. Pub. No. 2017/0137530, Armour, et al. (Eur. J. Immunol. 29(8) (1999) 2613-2624), Shields, et al. (J. Biol. Chem. 276(9) (2001) 6591-6604), and Oganesyan, et al. (Acta Cristallographica D64 (2008) 700-704), each herein incorporated by reference in its entirety. In specific embodiments, the antibody has one or more engineered mutations in an amino acid sequence of an antibody domain that reduce binding of an Fc portion of the ROR binding molecule by FcR receptors. In some embodiments, the FcR receptors are FcRγ receptors. In particular embodiments, the FcR receptors are FcγRIIa and/or FcγRIIIA receptors. In specific embodiments, the one or more engineered mutations that reduce effector function are mutations in a CH2 domain of an antibody.

6.3.2.1 Payloads

The protein constructs comprise a payload.

In various embodiments, the payload may comprise nucleotides, nucleotides that further comprise a detectable moiety or a toxin or that disrupts transcription, nucleic acids such as DNA, mRNA molecules that encode a polypeptide such as an enzyme, other RNA molecules (e.g., RNAi, miRNA, siRNA, piRNA, snoRNA, snRNA, exRNA, scaRNA and lncRNA), amino acids (e.g., amino acids comprising a detectable moiety or a toxin or that disrupt translation), polypeptides (e.g., enzymes, biologics), lipids, carbohydrates, small molecules (e.g., small molecule drugs and toxins) and combinations thereof.

In certain embodiments, the payload is a therapeutic agent. Therapeutic agents include, but are not limited to, chemotherapeutic agents, immunomodulators (e.g., cytokines, chemokines, or checkpoint inhibitors), hormones and toxins (e.g., cytotoxic agents).

In certain embodiments, the payload is an antibody. In an embodiment, the antibody comprises at least an antigen binding site (ABS) specific for a CD3 antigen. In an embodiment, the antibody comprises at least an ABS specific for a Tumor Necrosis Factor alpha (TNFα) antigen. In an embodiment, the antibody comprises an Fc domain capable of interaction with Fc receptors. In an embodiment, the antibody comprises an Fc domain incapable of interaction with Fc receptors.

In certain embodiments, the payload is a hormone. In certain embodiments, the payload is a dietary supplement. In certain embodiments, the payload is anti-microbial agent.

In certain embodiments, the protein constructs comprise a plurality of payloads that may be the same or different.

In particular embodiments, the payload is attached to the C-terminus of the BTNL3/8 targeting moiety. In particular embodiments, the payload is attached to the N-terminus of the BTNL3/8 targeting moiety.

6.3.1. Polypeptide

In various embodiments, the payload is a polypeptide. In certain embodiments, the payload is a polypeptide fused in-frame to the BTNL3/8 targeting moiety. In particular embodiments, the payload is fused in-frame to the C-terminus of the BTNL3/8 targeting moiety. In particular embodiments, the payload is fused in-frame to the N-terminus of the BTNL3/8 targeting moiety.

In certain embodiments, the polypeptide payload is a cytokine. In certain embodiments, the payload is an anti-inflammatory cytokine, such as interleukin 10 (IL-10), interleukin 22 (IL-22) or Transforming Growth Factor Beta (TGFβ).

In certain embodiments, the payload is an anti-proinflammatory polypeptide.

In particular embodiments, the anti-proinflammatory polypeptide is an inhibitor of one or more pro-inflammatory cytokines. In particular embodiments, the anti-proinflammatory polypeptide is an inhibitor of one or more of interleukin-1 (IL-1), IL-6, IL-12, IL-18, Tumor Necrosis Factor Alpha (TNFα), interferon gamma (INF-γ) or granulocyte-macrophage colony stimulating factor. In certain embodiments, the anti-proinflammatory polypeptide is a soluble cytokine receptors with anti-inflammatory activities, such as soluble Tumor Necrosis Factor receptor p55, Soluble Tumor Necrosis Factor, p75, Soluble IL-1 receptor type 2, IL-18 binding protein. In certain embodiments, the anti-proinflammatory polypeptide comprises an antibody antigen binding site that binds specifically to a proinflammatory cytokine.

In some embodiments, the payload is a peptide. In certain embodiments, the payload is a peptide fused in-frame to the BTNL3/8 targeting moiety.

6.3.2.1.1 Antibody Antigen Binding Site

In certain embodiments, the payload is at least one antibody antigen-binding site (ABS). In certain embodiments, the antibody antigen-binding site is formatted as a Fab fragment, Fv, scFv, tandem scFv, Diabody, scDiabody, DART, tandAb, minibody, camelid VHH, Nanobody, or other antibody fragments or formats known to those skilled in the art. Exemplary antibody and antibody fragment formats are described in detail in Brinkmann et al., *MABS*, 2017, Vol. 9, No. 2, 182-212), herein incorporated by reference for all that it teaches.

In various embodiments, the at least one antibody antigen-binding site is specific for a cytokine. In some embodiments, the antigen-binding site is specific for a pro-inflammatory cytokine. In particular embodiments, the at least one antigen-binding site is specific for interleukin-1 (IL-1), IL-6, IL-12, IL-18, Tumor Necrosis Factor Alpha (TNFα), interferon gamma (INF-γ) or granulocyte-macrophage colony stimulating factor.

In an embodiment, the antibody comprises at least an antigen binding site (ABS) specific for an anti-inflammatory cytokine such as interleukin 10 (IL-10), interleukin 22 (IL-22) or Transforming Growth Factor Beta (TGFβ). In an embodiment, the antibody comprises at least an antigen binding site (ABS) specific for an anti-proinflammatory agent.

In some embodiments, the antibody comprises at least an antigen binding site (ABS) specific for a cytokine antigen. In an embodiment, the antibody is comprises at least an ABS specific for a Tumor Necrosis Factor alpha (TNFα) antigen.

6.3.2. Small Molecule Payload

In certain embodiments, the payload is a small molecule. In certain embodiments, the small molecule is a therapeutic (i.e., small molecule drug). In certain embodiments, the small molecule therapeutic is an immunomodulator. In certain embodiments, the small molecule is an inhibitor or activator of a cellular protein (e.g., a receptor, other signaling molecule, enzyme or transcription factor). In certain embodiments, the small molecule therapeutic is a toxin.

In some embodiments, the payload is a drug that is linked to the BTNL3/8 targeting moiety by chemical conjugation.

Methods of preparing antibody-drug conjugates (ADCs) that can be adapted to conjugate drugs to the protein constructs disclosed herein are described, e.g., in U.S. Pat. No. 8,624,003 (pot method), U.S. Pat. No. 8,163,888 (one-step), U.S. Pat. No. 5,208,020 (two-step method), U.S. Pat. Nos. 8,337,856, 5,773,001, 7,829,531, 5,208,020, 7,745, 394, WO 2017/136623, WO 2017/015502, WO 2017/015496, WO 2017/015495, WO 2004/010957, WO 2005/077090, WO 2005/082023, WO 2006/065533, WO 2007/030642, WO 2007/103288, WO 2013/173337, WO 2015/057699, WO 2015/095755, WO 2015/123679, WO 2015/157286, WO 2017/165851, WO 2009/073445, WO 2010/068759, WO 2010/138719, WO 2012/171020, WO 2014/008375, WO 2014/093394, WO 2014/093640, WO 2014/160360, WO 2015/054659, WO 2015/195925, WO 2017/160754, Storz (*MAbs*. 2015 Nov.-Dec.; 7(6): 989-1009), Lambert et al. (*Adv Ther*, 2017 34: 1015), Diamantis et al.

(*British Journal of Cancer*, 2016, 114, 362-367), Carrico et al. (*Nat Chem Biol*, 2007. 3: 321-2), We et al. (*Proc Natl Acad Sci USA*, 2009. 106: 3000-5), Rabuka et al. (*Curr Opin Chem Biol.*, 2011 14: 790-6), Hudak et al. (*Angew Chem Int Ed Engl.*, 2012: 4161-5), Rabuka et al. (*Nat Protoc.*, 2012 7:1052-67), Agarwal et al. (*Proc Natl Acad Sci USA.*, 2013, 110: 46-51), Agarwal et al. (*Bioconjugate Chem.*, 2013, 24: 846-851), Barfield et al. (*Drug Dev. and D.*, 2014, 14:34-41), Drake et al. (*Bioconjugate Chem.*, 2014, 25:1331-41), Liang et al. (*J Am Chem Soc.*, 2014, 136:10850-3), Drake et al. (*Curr Opin Chem Biol.*, 2015, 28:174-80), and York et al. (*BMC Biotechnology*, 2016, 16(1):23), each of which is hereby incorporated by reference in its entirety for all that it teaches.

6.3.3. Nucleic Acid Payload

In certain embodiments, the payload is a nucleic acid. The nucleic acids can be DNA or RNA such as, but not limited to, dsDNA, mRNA, miRNA, lncRNA and siRNA, piRNA, snoRNA, snRNA, exRNA and scaRNA.

6.3.3.1 Optional Linker

The protein constructs described herein optionally comprise a linker linking the targeting moiety to the payload.

In some embodiments, the optional linker is a peptide fused in-frame to the targeting moiety. In an embodiment, the optional linker is fused in frame to the C-terminus of the targeting moiety. In an embodiment, the optional linker is fused in frame to the N-terminus of the targeting moiety.

In some embodiments, the optional linker is a molecule conjugated to the targeting moiety. In various embodiments, the protein construct has modifications that comprise functional groups or chemically reactive groups that can be used in downstream processes, such as linking to additional functional elements (e.g., payload, and BTNL3/8 targeting moiety) and downstream purification processes. In certain embodiments, the linker comprises a cleavable molecule (e.g., a peptide that can be cleaved by a site-specific protease, or other molecule that allows for cleavage of the linker into two or more fragments). In certain embodiments, the modifications are chemically reactive groups including, but not limited to, reactive thiols (e.g., maleimide based reactive groups), reactive amines (e.g., N-hydroxysuccinimide based reactive groups), "click chemistry" groups (e.g., reactive alkyne groups), and aldehydes bearing formylglycine (FGly). In certain embodiments, the modifications are functional groups including, but not limited to, affinity peptide sequences (e.g., HA, HIS, FLAG, GST, MBP, and Strep systems etc.). In certain embodiments, the functional groups or chemically reactive groups have a cleavable peptide sequence. In particular embodiments, the cleavable peptide is cleaved by means including, but not limited to, photocleavage, chemical cleavage, protease cleavage, reducing conditions, and pH conditions. In particular embodiments, protease cleavage is carried out by intracellular proteases. In particular embodiments, protease cleavage is carried out by extracellular or membrane associated proteases. ADC therapies adopting protease cleavage are described in more detail in Choi et al. (*Theranostics*, 2012; 2(2): 156-178.), the entirety of which is hereby incorporated by reference for all it teaches.

In certain embodiments, in addition to linking the targeting moiety to the payload, the linker can be used to allow site-specific conjugation of a molecule to a functional element (e.g., a targeting moiety or a payload) of the protein construct. In certain embodiments, the linker may additionally be used to identify or detect the protein construct in vitro or in vivo.

In certain embodiments, the protein construct comprises more than one optional linker.

6.4. Other Targeting Moieties

In certain aspects, described herein is a panel or library of recombinant homodimer and heterodimer human γδ TCRs and methods to use this panel or library to identify specific cognate human binding domains or partners that determine or assist tissue specific distribution of γδ T cells. These binding partners are often termed human innate 'self-antigens' and until the discoveries described herein have been very difficult/impossible to determine or characterize further. In an aspect of the invention, we describe recombinant human γδ TCR proteins that exhibit similar tissue specificity or binding as that exhibited in their natural cellular environment. In a further aspect of this invention, we describe a method of (i) generating at least one recombinant γδ TCR (ii) displaying or presenting or mixing this recombinant protein or proteins with a potential cognate binding partner or partners, preferably expressed on a cell surface and (iii) identifying or validating specific γδ TCR/binding partner interaction accordingly. In an aspect of the invention, the resulting γδ TCR identified or sequence derivatives therefrom is employed as a targeting moiety to deliver a therapeutic payload to target tissues or cells expressing the cognate binding partner. In a further embodiment, cells expressing the identified cognate binding partner identified by methods described herein are then targeted with an alternative targeting moiety such as an antibody or derivative therefrom.

6.5. Methods of Manufacturing

The protein constructs described herein can readily be manufactured by expression using standard cell free translation, transient transfection, and stable transfection approaches currently used for T-cell receptor or antibody manufacture.

6.6. Methods of Purification

Appropriate purification methods known to those skilled in the art, can be used to purify the protein construct. Expressed proteins can be readily separated from undesired proteins and protein complexes using an affinity resin (e.g., that binds an affinity tag on the protein construct). Further purification can be effected using ion exchange chromatography as is routinely used in the art.

Methods to assess the efficacy and efficiency of purification steps are well known to those skilled in the art and include, but are not limited to, SDS-PAGE analysis, ion exchange chromatography, size exclusion chromatography, and mass spectrometry. Purity can also be assessed according to a variety of criteria. Examples of criterion include, but are not limited to: 1) assessing the percentage of the total protein in an eluate that is provided by the completely assembled protein construct 2) assessing the fold enrichment or percent increase of the method for purifying the desired products, e.g., comparing the total protein provided by the completely assembled protein construct in the eluate to that in a starting sample, 3) assessing the percentage of the total protein or the percent decrease of undesired products, e.g., the incomplete complexes described above, including determining the percent or the percent decrease of specific undesired products (e.g., unassociated single polypeptide chains, dimers of any combination of the polypeptide chains, or trimers of any combination of the polypeptide chains).

6.7. Pharmaceutical Compositions

In another aspect, pharmaceutical compositions are provided that comprise a protein construct comprising a BTNL3/8 targeting moiety and a payload as described herein and a pharmaceutically acceptable carrier or diluent. In typical embodiments, the pharmaceutical composition is sterile. In certain aspects, described herein are pharmaceutical compositions comprising any one of the above mentioned protein constructs and a pharmaceutically acceptable carrier.

In an embodiment, the pharmaceutical composition is suitable for parenteral administration. In an embodiment, the administration is intravenous administration. In an embodiment, the administration is intramuscular administration. In an embodiment, the administration is sub-cutaneous administration.

In various embodiments, the pharmaceutical composition comprises the protein construct at a concentration of 0.1 mg/ml-100 mg/ml. In specific embodiments, the pharmaceutical composition comprises the protein construct at a concentration of 0.5 mg/ml, 1 mg/ml, 1.5 mg/ml, 2 mg/ml, 2.5 mg/ml, 5 mg/ml, 7.5 mg/ml, or 10 mg/ml. In some embodiments, the pharmaceutical composition comprises the protein construct at a concentration of more than 10 mg/ml. In certain embodiments, the protein construct is present at a concentration of 20 mg/ml, 25 mg/ml, 30 mg/ml, 35 mg/ml, 40 mg/ml, 45 mg/ml, or even 50 mg/ml or higher. In particular embodiments, the protein construct is present at a concentration of more than 50 mg/ml.

In various embodiments, the pharmaceutical compositions are described in more detail in U.S. Pat. Nos. 8,961,964, 8,945,865, 8,420,081, 6,685,940, 6,171,586, 8,821,865, 9,216,219, U.S. application Ser. No. 10/813,483, WO 2014/066468, WO 2011/104381, and WO 2016/180941, each of which is incorporated herein in its entirety.

6.8. Compositions for Use

In an aspect, compositions for use are also provided. In one embodiment, there is provided a composition comprising a protein construct comprising a BTNL3/8 targeting moiety and payload as described herein, for use in therapy. The composition may be used in the treatment of, e.g., inflammatory conditions, inflammatory bowel disease, irritable bowel syndrome, diverticulitis, celiac disease, metabolic disorders, cancer, immune related disorders, autoimmunity, transplantation rejection, post-traumatic immune responses, graft-versus-host disease, ischemia, stroke, and infectious diseases.

In an aspect, use of compositions for the manufacture of a medicament are also provided. In one embodiment, there is provided the use of a composition comprising a protein construct comprising a BTNL3/8 targeting moiety and payload as described herein, for the manufacture of a medicament for the treatment of, e.g., inflammatory conditions, inflammatory bowel disease, irritable bowel syndrome, diverticulitis, celiac disease, metabolic disorders, cancer, immune related disorders, autoimmunity, transplantation rejection, post-traumatic immune responses, graft-versus-host disease, ischemia, stroke, and infectious diseases.

6.9. Methods of Treatment

In an aspect, methods of treatment are provided, the methods comprising administering a protein construct comprising a BTNL3/8 targeting moiety and payload as described herein to a patient in an amount effective to treat the patient. A protein construct of the present disclosure may be administered to a subject per se or in the form of a pharmaceutical composition for the treatment of, e.g., inflammatory conditions, inflammatory bowel disease, irritable bowel syndrome, diverticulitis, celiac disease, metabolic disorders, cancer, immune related disorders, autoimmunity, transplantation rejection, post-traumatic immune responses, graft-versus-host disease, ischemia, stroke, and infectious diseases.

6.9.1.1 Conditions of the Gastrointestinal System

In certain aspects, described herein are methods of treating a condition of the gastrointestinal system. Conditions of the gastrointestinal system, include, but are not limited to, immune-related conditions of the gastrointestinal system, inflammatory conditions of the gastrointestinal system, microbial infection of tissues of the gastrointestinal system and conditions caused by dietary abnormalities, metabolic disorders or deficiencies. Conditions of the gastrointestinal system include, but are not limited to, inflammatory bowel disease, celiac disease, irritable bowel syndrome, diverticulitis, Crohn's disease, and cancer (e.g., colon cancer, rectal cancer, stomach cancer). In certain aspects, described herein are methods of treating a condition of the gastrointestinal system in which gastrointestinal tissue expresses BTNL3/8, comprising: administering a therapeutically effective amount of the pharmaceutical composition to a patient with the condition in which the gastrointestinal tissue expresses BTNL3/8. In an embodiment of the method, the payload of the protein construct is an anti-inflammatory agent. In an embodiment, the anti-inflammatory agent is an aminosalicylate. In an embodiment, the anti-inflammatory agent is a non-steroidal anti-inflammatory agent. In an embodiment, the anti-inflammatory agent is an anti-inflammatory cytokine, optionally interleukin 10 (IL-10), interleukin 22 (IL-22) or Transforming Growth Factor Beta (TGFβ). In an embodiment, the anti-inflammatory agent is an anti-proinflammatory agent. In an embodiment, the anti-inflammatory agent is a steroid. In an embodiment, the steroid is a glucocorticoid. In an embodiment, the glucocorticoid is prednisone. In an embodiment, the glucocorticoid is hydrocortisone. In an embodiment, the payload is an immunomodulator.

6.9.2.1 Inflammatory Bowel Disease

In certain aspects, described herein are methods of treating an inflammatory bowel disease, comprising administering a therapeutically effective amount of any of the above mentioned pharmaceutical compositions to a patient with inflammatory bowel disease. In an embodiment, the inflammatory bowel disease is ulcerative colitis. In an embodiment, the inflammatory bowel disease is Crohn's disease. In an embodiment, the payload of the protein construct is an anti-inflammatory agent. In an embodiment, the anti-inflammatory agent is an aminosalicylate. In an embodiment, the anti-inflammatory agent is a non-steroidal anti-inflammatory. In an embodiment, the anti-inflammatory agent is an anti-inflammatory cytokine, optionally interleukin 10 (IL-10), interleukin 22 (IL-22) or Transforming Growth Factor Beta (TGFβ). In an embodiment, the anti-inflammatory agent payload is an anti-proinflammatory agent. In an embodiment, the anti-inflammatory agent payload is a steroid. In an embodiment, the steroid is a glucocorticoid. In an embodiment, the glucocorticoid is prednisone. In an embodiment, the glucocorticoid is hydrocortisone. In an embodiment, the payload of the protein construct is an antibiotic. In an embodiment, the antibiotic payload is rifaximin, ciprofloxacin, metronidazole, moxifloxacin or amoxicillin. In an embodiment, the payload of the protein construct is a calcineurin inhibitor. In an embodiment, the calcineurin inhibitor is cyclosporine A or tacrolimus. In an embodiment, the payload of the protein construct is an immunomodulator. In an embodiment, the immunomodulator is an immune suppressor. In an embodiment, the immune suppressor is azathioprine, 6-mercaptopurine, methotrexate or thiopurine. In an embodiment, the payload of the protein construct is a protein payload. In an embodiment, the protein payload is an antibody, an antibody fragment or a single chain variable fragment. In an embodiment, the protein payload comprises and at least an ABS specific for a TNFα antigen. In an embodiment, the protein payload comprises the complementarity-determining regions (CDRs) of adalimumab, infliximab or certolizumab. In an embodiment, the protein payload comprises at least an ABS specific for an interleukin antigen. In an embodiment, the interleukin is IL-12, IL-23, or combinations thereof. In an embodiment, the protein payload comprises the CDRs of ustekinumab or brikinumab. In an embodiment, the biologic payload comprises at least an ABS specific for an integrin antigen. In an embodiment, the integrin is alpha 4 integrin. In an embodiment, the protein payload comprises the CDRs of infliximab, natalizumab or vedolizumab. In an embodiment, the protein construct comprises an analgesic payload. In an embodiment, the protein construct comprises a dietary supplement payload.

6.9.3.1 Infection

In certain aspects, described herein are methods of treating a microbial infection, comprising administering a therapeutically effective amount of any one of the above mentioned pharmaceutical compositions to a patient with the microbial infection. In certain embodiments, the payload is an anti-microbial agent. In certain embodiments, the anti-microbial agent is an anti-parasitic agent, an antibiotic, an anti-fungal agent or an anti-viral agent.

6.9.4.1 Metabolic Disorder or Deficiency

In certain aspects, described herein are methods of treating a metabolic disorder or metabolic deficiency, comprising administering a therapeutically effective amount of any one of the above mentioned pharmaceutical compositions to a patient with the metabolic disorder or metabolic deficiency. In certain embodiments, the payload is a dietary supplement. In certain embodiments, the dietary supplement is an enzyme or a vitamin.

6.9.5.1 Modulating the Immune System

In certain aspects, described herein are methods of modulating the immune system, comprising administering a therapeutically effective amount of any one of the above mentioned pharmaceutical compositions to a patient with an immune-related condition. In certain embodiments, the payload is an immune suppressor. In certain embodiments, the immune suppressor is azathioprine, 6-mercaptopurine, methotrexate or thiopurine. In certain embodiments, the payload is an immune stimulator. In certain embodiments, the immune stimulator is a cytokine.

6.10. Examples

The following examples are provided by way of illustration, not limitation.

6.10.1.1 Methods

Non-limiting, illustrative, methods for the design and analysis of protein constructs comprising BTNL3/8 targeting moieties that comprise a TCR Vγ domain are described below. Methods for primary lymphocyte isolation, co-culture with BTNL3/8 expressing HEK293 cells and deep sequencing are also described in Di Marco Barros et al., Cell. 2016, (167), pp. 203-218.

Human Samples and Primary Lymphocyte Isolation

Endoscopic biopsies were obtained from the ascending colon of adult donors undergoing routine diagnostic colonoscopy. Primary gut lymphocytes were obtained using an adaptation of the method of Clark et al., 2006, J. Invest. Dermatol. (126), pp. 1059-1070. Biopsies were washed for 20 min in 5 mL wash medium (RPMI 1640 10% FCS, 0-mercaptoethanol, penicillin [500 U/ml], streptomycin [500 mg/ml], metronidazole [5 mg/ml, Pharmacy department, Guy's Hospital], gentamicin [100 mg/ml, Sigma-Aldrich] and amphotericin 12.5 mg/ml [Thermo Fisher Scientific]). One endoscopic biopsy was placed on top of each matrix, which was inverted, and pressure applied, to crush the biopsy into the matrix. The matrices were placed into a 24-well plate (1 per well) and covered with 2 mL RPMI 1640 (supplemented with 10% FCS, β-mercaptoethanol, penicillin [100 U/ml], streptomycin [100 mg/ml], metronidazole [1 mg/ml], gentamicin [20 mg/ml], amphotericin [2.5 mg/ml]), IL-2 (100 U/mL, Novartis Pharmaceutical UK) and IL-15 (10 ng/mL, Biolegend). 1 ml of medium was aspirated every second day and replaced with complete medium containing 2× concentrated cytokines. Cells were harvested and residual biopsy and empty wells were washed with PBS 0.02 mM HEPES. The cell suspension was passed through a 70 mm nylon cell strainer, centrifuged at 400 g for 5 min and resuspended in complete medium without additional cytokine and placed into co-culture immediately. Lymphocytes were used after 5-7 days of culture. PBMC were isolated by Ficoll gradient from blood obtained from the blood donation service.

HEK293T Co-Culture Assay $5 \times 10^5$ HEK293T cells, transduced with either empty vector (EV), BTNL3, BTNL8 or BTNL3+8 and $2 \times 10^5$ freshly harvested primary human lymphocytes were co-cultured in 96-well plates with complete medium without supplementary cytokine and incubated at 37° C. at 5% $CO_2$ for 16 hrs.

Deep Sequencing

Mouse TRDV gene amplification and sequencing of TCRδ CDR3 from RNA purified from sorted Vγ7+IEL was performed using the Amp2Seq Platform (iRepertoire).Human TCRG Vγ gene: Amplification and sequencing of TCRγ CDR3 was performed using the immunoSEQ Platform (Adaptive Biotechnologies).

Design of Soluble γδTCR Heterodimers

The design of the soluble γδTCR heterodimers comprising the T cell receptor α and T cell receptor β constant regions used in the below Examples were generated according to Xu et al., PNAS, 2011 Vol. 108; pp. 2414-2419.

Figure 2:
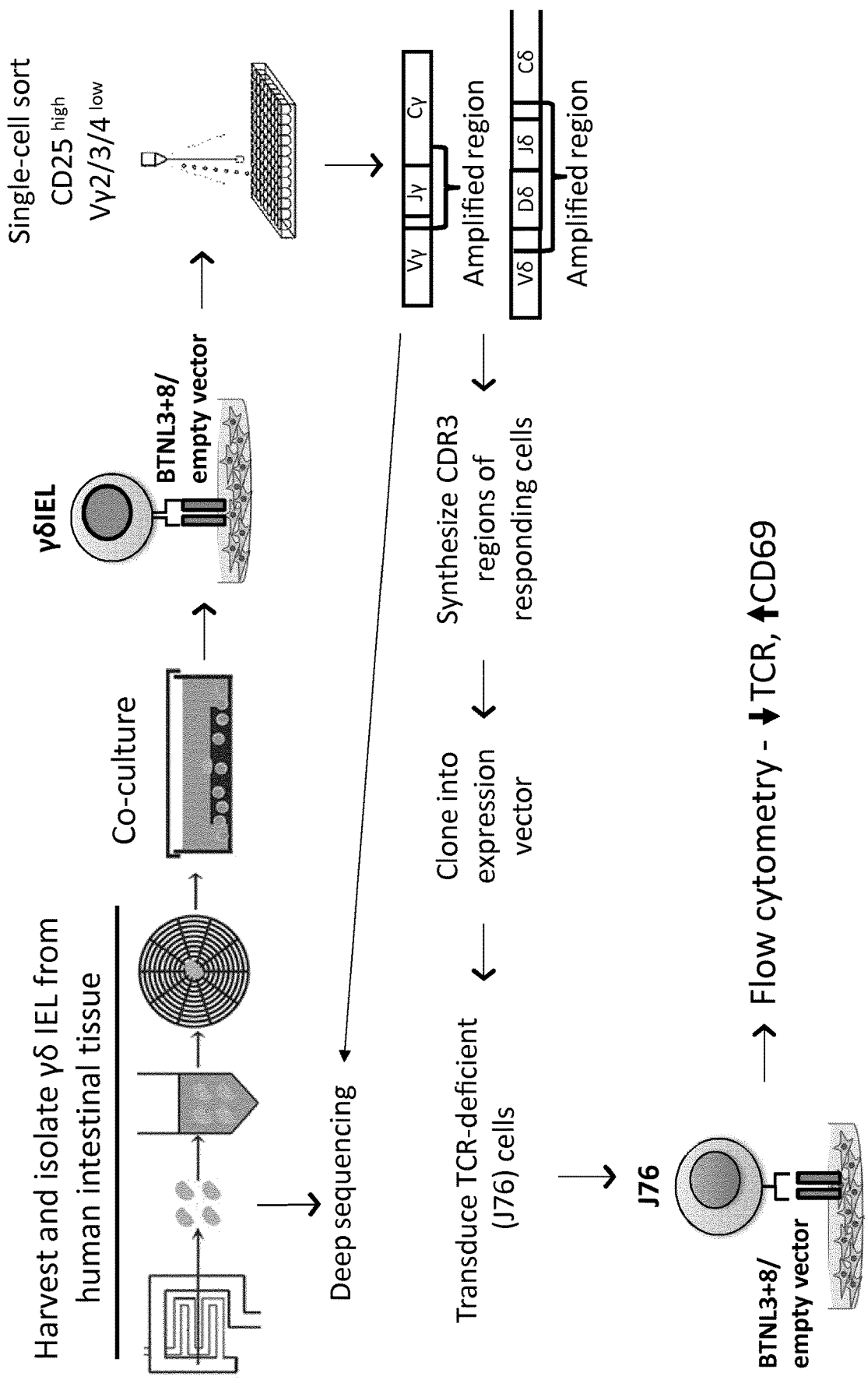
FIG. 2 depicts the experimental approach used to identify, clone and test γδ T cell receptors isolated from responding intraepithelial leukocytes (IEL).
Figure 3A:
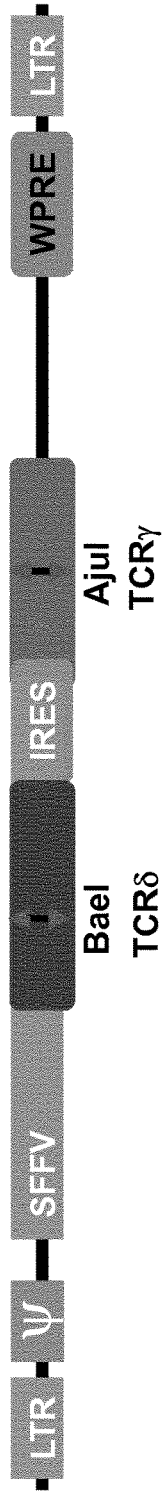
FIG. 3A is a diagram of the lentiviral vector backbone used for expression of the γδ TCR variable domains derived from the isolated IELs in a TCR construct in TCR-deficient Jurkat cells.
Figure 3B:
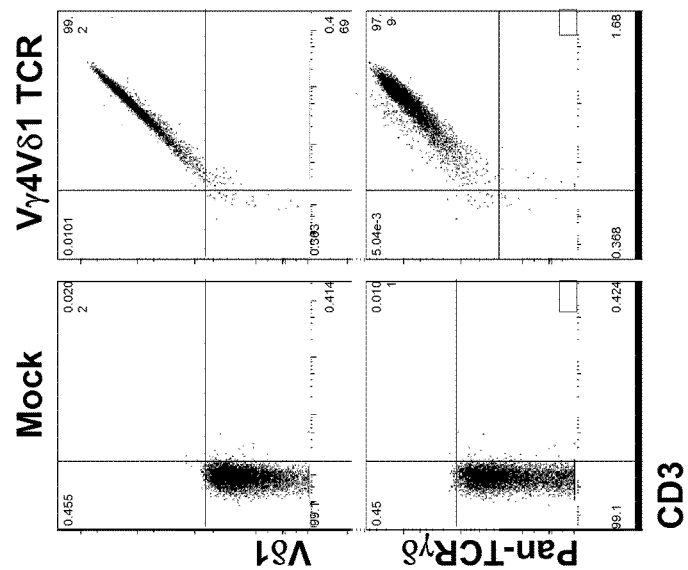
FIG. 3B shows expression 72 h post-transduction of a TCR construct that has a cloned CDR3 pair from the γδ TCR variable domains in TCR-deficient Jurkat (J76 cells).

6.10.2.1 Example 1: γ6TCR Variable Regions Isolated from Intraepithelial Leukocytes Derived from Human Intestinal Tissue Confer BTNL3/8 Induced Activity of TCRs The TCR variable region of intraepithelial leukocytes (IEL) derived from human intestines and that are responsive to BTNL3/8 were cloned and expressed in TCR-deficient cells (FIG. 2). IELs were isolated from human intestine tissue and co-cultured with HEK293T cells co-overexpressing BTNL3/8. Responsive IELs that exhibited TCR activation (high expression of CD25 and down-regulation Vγ) were then single cell sorted. The variable region of the γ chain and δ chain were amplified and cloned into a lentiviral expression vector (FIG. 3A). TCR-deficient Jurkat cells (J76 cell line) were transduced and co-cultured with HEK293T cells expressing BTNL3/8 (FIG. 3B). The J76 cells were then sorted for TCR activation (CD69 expression and TCR down-regulation) (FIG. 4A). Anti-CD3 antibody was used as a positive control for TCR activation. When co-cultured with BTNL3/8 expressing cells, J76 cells expressing the transduced TCR (H7 TCR) harboring a Vγ4 and Vδ1 domains exhibited increased CD69 expression and down-regulated γδ TCR. Three independent J76 lines, B3, C11 and H7, transduced with Vγ4Vδ1 that represent three different CDR3 pairs obtained with the method shown in FIG. 2, but not a Vγ9Vδ2 line (Vγ9Vδ2), responded to BTNL3/8-expressing cells (FIG. 4B). These results show that the Vγ4Vδ1 domains of human IELs are sufficient to confer TCR responsiveness to BTNL3/8.

6.10.3.1 Example 2: The Cdr4 of Vγ4 is Required for TCR Responsiveness to BTNL3/8

To identify the Vγ4 region that is critical for responsiveness to BTNL3/8, the entire Vγ4 domain of the H7 responsive TCR line was substituted with a Vγ2 region (FIG. 5). The fold change (FC) in % CD69 expression and the percent TCR downregulation in transduced J76 cells expressing the Vγ4 TCR (H7 WT) or Vγ2 substituted TCR upon co-culture with HEK293T expressing BTNL3/8 was determined. When the full V region of the responding Vγ4 H7 TCR is replaced by a Vγ2-coding sequence (Vγ2 H7) (CDR3gamma and full delta chain not replaced), TCR activation by the BTNL3/8 expressing cells was lost. However, when the CDR1 (H7 CDR1$^{Vγ2}$) and/or the CDR2 (H7 CDR2$^{Vγ2}$) of the responding Vγ4 H7 TCR was replaced by a Vγ2-coding sequence, the TCR activation by the BTNL3/8 expressing cells was retained. These results indicate that the CDR4 is required for the TCR response to BTNL3/8.

To further elucidate the region within the Vγ4 that is essential for responding to BTNL3/8, two pairs of amino acids located with the CDR4 were substituted with the Vγ2 sequence (FIGS. 6 and 7). The fold change (FC) in % CD69 expression in transduced cells and the percent TCR down-regulation in J76 cells expressing Vγ4 TCR (H7 WT), Vγ2 TCR with the H7 CDR3 (Vγ2 H7), and Vγ4 TCR with amino acid substitutions within the CDR4 upon co-culture with HEK293T cells expressing BTNL3/8 was determined (FIG. 7). YA substitutions at amino acid positions 87 and 90 abrogated TCR activation by the BTNL3/8 expressing cells; whereas NL substitutions at amino acid positions 94 and 98 did not abrogate TCR activation by the BTNL3/8 expressing cells. These results confirm that the amino acids at positions 87 and 90 of the CDR4 region of the Vγ4 TCR is essential for TCR responsiveness to BTNL3/8.

6.10.4.1 Example 3: Soluble TCR Vγ4/Vδ Heterodimers Bind to BTNL3/8-Expressing Cells Soluble Vγ/VS TCR heterodimers were expressed and stabilized by leucine zipper complementarity (FIG. 8). Vγ or Vδ domains were fused in-frame to a TCRα or TCRβ constant region lacking the transmembrane domain, followed by a leucine zipper sequence and a histidine tag/linker. The Vγ4/VS1 heterodimer corresponds to SEQ ID NOs:10 and 9. The Vγ4/VS2 heterodimer corresponds to SEQ ID NOs: 10 and 11. The Vγ2/VS1 heterodimer corresponds to SEQ ID NOs:12 and 9. The Vγ8/VS1 heterodimer corresponds to SEQ ID NOs: 13 and 9.

The soluble TCRs were used to stain HEK293T cells transduced with Flag-BTNL3+HA-BTNL8 or empty vector (FIG. 10). Vγ4/VS1 soluble TCR and Vγ4/Vδ2 soluble TCR show strong binding to BTNL3+BTNL8-expressing but not empty vector (EV) control cell lines. The results demonstrate that soluble TCRs expressing Vγ4/VS1 domains or Vγ4/Vδ2 domains bind to BTNL3/8 expressing cells, but not to cells lacking BTNL3/8. Taken together, the results demonstrate that the Vγ4 CDR4 is essential for the BTNL3/8-induced TCR response, and also suggests that the Vγ4 CDR4 interacts with BTNL3/8.

To further evaluate the binding of soluble Vγ4+TCR constructs to cells expressing BTNL3+8, HEK293T cells were transduced with pCSIGPW encoding the indicated BTNL3 and BTNL8 constructs or empty vector (EV). Cells were then stained with a soluble His-tagged Vγ4δ2 TCR for 45 minutes at 4° C., washed twice, stained with APC anti-His tag antibody (α-His) for 45 minutes at 4° C., washed twice again, and then analyzed by flow cytometry (FIG. 9A). Cell populations represented in FIG. 9B were stained in parallel with anti-FLAG and anti-HA antibodies to verify that the lack of soluble TCR binding was not due to a failure to express the BTNL3+8 constructs. The results demonstrate the ability of a soluble TCR construct to bind cells expressing BTNL3+BTNL8, but not to any of the IgV-domain mutants previously described to fail to induce a response by Vγ4+ T cells (e.g., L3$^{GQFSS}$, L3$^{RI}$, L3$^{YQKAI}$). See Melandri, et al. Nat. Immunol. 2018, which is hereby incorporated by reference in its entirety.

6.10.5.1 Example 4: Soluble TCR Bound to BTNL3/8-Expressing Cells is Internalized To determine whether a soluble TCR bound to the surface of cells expressing BTNL3+BTNL8 is internalized, HEK293T cells transduced to express wild-type BTNL3 and BTNL8 (293T.L3L8) were stained with soluble His-tagged Vγ4Vδ2 TCR at 37° C. for up to 120 minutes (FIG. 11B). 293T.L3L8 cells stained with soluble His-tagged Vγ4Vδ2 TCR at 4° C. for 120 minutes served as a control as the low temperature prevented internalization (FIG. 11A). Cells were subsequently stained with APC α-His tag antibody (α-His) for 45 minutes at 4° C. Results show a decrease in the APC signal over time in cell populations incubated at 37° C., demonstrating that cells rapidly internalize the soluble TCR construct (FIG. 12).

To determine whether internalization of the soluble TCR is specific or is the result of rapid cycling of cell surface BTNL molecules, the experiment was repeated to compare soluble TCR with an anti-BTNL3 antibody (Rabbit polyclonal, Aviva Biosystems) (reference included). HEK293T cells transduced with an empty vector (293T.EV) were used as a negative control for staining with α-BTNL3. HEK293T cells transduced with the BTNL3 construct L3^RIL8 (293T.L3^RIL8) were used as a negative control for staining with soluble TCR. The results show that α-BTNL3 staining is identical at 4° C. and 37° C., demonstrating that while the α-BTNL3 specifically binds to cells that express BTNL3/8, the antibody stays on the surface of the cell (FIG. 13A). Quantification of the results is shown in FIG. 13B.

6.10.6.1 Example 5: Soluble TCR Delivers a Payload to BTNL3/8-Expressing Cells To determine whether a payload may be delivered intracellularly via soluble TCR binding to BTNL3/8-expressing cells, 293T.L3L8 or 293T.L3^RIL8 cells were incubated with soluble TCR pre-labeled with an APC α-His tag antibody on the carboxy-terminal end of the soluble TCR construct. Either 3 or 10 μg/mL of the complex was incubated for 1 hour at either 4° C. or 37° C. Cells were then washed and treated for 15 minutes with trypsin or DMEM (control) as depicted in FIG. 14. Results show that the fraction of soluble TCR+α-His signal (APC fluorescence) is greater after trypsin treatment when cells were incubated with complexes at 37° C. and protected from trypsin by internalization of the complex, compared to 4° C. (FIG. 15A). Thus, the results demonstrate that soluble TCR internalization may be used as a means to deliver payloads intracellularly to BTNL3/8-expressing cells. Quantification of the results is shown in FIG. 15B.

Image Cytometry was used to visualize the soluble TCR-mediated intracellular delivery of the APC α-His antibody payload. 293T.L3^RIL8 or 293T.L3L8 cells were incubated with soluble TCR+α-His antibody complexes for 1 hour at 4° C. or 37° C. Following treatment with DMEM or trypsin (as previously described), cells were fixed and permeabilized (FIG. 16A) or fixed, permeabilized, and stained with the late endosomal marker CD107a (FIGS. 16B and 16C). Image Cytometry of the negative controls permitted evaluation of background APC signal (FIG. 16A). Image Cytometry results of cells incubated with TCR+α-His antibody complexes demonstrate that the complexes are mostly bound to the cell surface when incubated with cells at 4° C. as the complexes can be visualized around the cells following treatment with DMEM whereas the signal is completely lost following treatment with trypsin (FIG. 16B). Complexes incubated with cells at 37° C., however, are detected in intracellular regions proximal to CD107a+ compartments following trypsin treatment (FIG. 16C)

6.11. Sequences

> Human Vγ4 amino acids 87-90
[SEQ ID NO: 1]
DTYG

> Mouse Vγ7 amino acids 87-90
[SEQ ID NO: 2]
HVYE

> Human Vγ4 domain CDR4 amino acids 85-100
[SEQ ID NO: 3]
KYDTYGSTRKNLRMIL

> Mouse Vγ7 domain CDR4 amino acids 85-100
[SEQ ID NO: 4]
KYHVYEGPDKRYKFVL

> Human Vγ2 domain CDR4 amino acids 85-100
[SEQ ID NO: 5]
KYYTYASTRNNLRLIL

> Human Vγ4 amino acids 19-118
[SEQ ID NO: 6]
SSNLEGRTKSVIRQTGSSAEITCDLAEGSTGYIHWYLHQEGKAPQRLLYY
DSYTSSVVLESGISPGKYDTYGSTRKNLRMILRNLIENDSGVYYCATWDG Human Vγ2 amino acids 19-118
[SEQ ID NO: 7]
SSNLEGRTKSVIRQTGSSAEITCDLAEGSNGYIHWYLHQEGKAPQRLQYY
DSYNSKVVLESGVSPGKYYTYASTRNNLRLILRNLIENDSGVYYCATWDG > Mouse Vγ7 amino acids 19-118
[SEQ ID NO: 8]
SSNLEERIMSITKLEGSSAIMTCDTHR-TGTYIHWYRFQKGRAPEHLLYY
NFVSSTTVVDSRFNSEKYHVYEGPDKRYKFVLRNVEESDSALYYCASWA- > Human Vδ1 with CDR3 from crystal structure 3OMZ fused in frame with TCR α Constant region, leucine zipper and C-terminal His tag
[SEQ ID NO: 9]
AQKVTQAQSSVSMPVRKAVTLNCLYETSWWSYYIFWYKQLPSKEMIFLIR
QGSDEQNAKSGRYSVNFKKAAKSVALTISALQLEDSAKYFCALGESLTRA
DKLIFGKGTRVTVEPNIQNPDPAVYQLRDSKSSDKSVCLFTDFDSQTNVS
QSKDSDVYITDKTVLDMRSMDFKSNSAVAWSNKSDFACANAFNNSIIPED
TFFPSPESSCTTAPSAQLKKKLQALKKKNAQLKWKLQALKKKLAQGSGHH
HHHH > Human Vγ4 with CDR3 from crystal structure 4MNH, fused with TCR β Constant region, leucine zipper
[SEQ ID NO: 10]
SSNLEGRTKSVIRQTGSSAEITCDLAEGSTGYIHWYLHQEGKAPQRLLYY
DSYTSSVVLESGISPGKYDTYGSTRKNLRMILRNLIENDSGVYYCATWDE
KYYKKLFGSGTTLVVTEDLKNVFPPEVAVFEPSEAEISHTQKATLVCLAT
GFYPDHVELSWWVNGKEVHSGVSTDPQPLKEQPALNDSRYALSSRLRVSA
TFWQNPRNHFRCQVQFYGLSENDEWTQDRAKPVTQIVSAEAWGRADCTTA
PSAQLEKELQALEKENAQLE > Human Vδ2 with CDR3 from crystal structure 3OMZ fused in frame with TCR α Constant region, leucine zipper and C-terminal His tag
[SEQ ID NO: 11]
AIELVPEHQTVPVSIGVPATLRCSMKGEAIGNYYINWYRKTQGNTITFIY
REKDIYGPGFKDNFQGDIDIAKNLAVLKILAPSERDEGSYYCALGESLTR
ADKLIFGKGTRVTVEPNIQNPDPAVYQLRDSKSSDKSVCLFTDFDSQTNV
SQSKDSDVYITDKTVLDMRSMDFKSNSAVAWSNKSDFACANAFNNSIIPE
DTFFPSPESSCTTAPSAQLKKKLQALKKKNAQLKWKLQALKKKLAQGSGH
HHHHH > Human Vγ2 with CDR3 from crystal structure 4MNH, fused with TCR β Constant region, leucine zipper
[SEQ ID NO: 12]
SSNLEGRTKSVIRQTGSSAEITCDLAEGSNGYIHWYLHQEGKAPQRLQYY
DSYNSKVVLESGVSPGKYYTYASTRNNLRLILRNLIENDSGVYYCATWDE -continued

KYYKKLFGSGTTLVVTEDLKNVFPPEVAVFEPSEAEISHTQKATLVCLAT

GFYPDHVELSWWVNGKEVHSGVSTDPQPLKEQPALNDSRYALSSRLRVSA

TFWQNPRNHFRCQVQFYGLSENDEWTQDRAKPVTQIVSAEAWGRADCTTA

PSAQLEKELQALEKENAQLEWELQALEKELAQ

> Human Vγ8 with CDR3 from crystal structure 4MNH, fused with TCR β Constant region, leucine zipper
[SEQ ID NO: 13]

SSNLEGRTKSVTRPTGSSAVITCDLPVENAVYTHWYLHQEGKAPQRLLYY

DSYNSRVVLESGISREKYHTYASTGKSLKFILENLIERDSGVYYCATWDE

KYYKKLFGSGTTLVVTEDLKNVFPPEVAVFEPSEAEISHTQKATLVCLAT

GFYPDHVELSWWVNGKEVHSGVSTDPQPLKEQPALNDSRYALSSRLRVSA

TFWQNPRNHFRCQVQFYGLSENDEWTQDRAKPVTQIVSAEAWGRADCTTA

PSAQLEKELQALEKENAQLEWELQALEKELAQ

> Leader sequence of Human Vγ4
[SEQ ID NO: 14]

MAWALAVLLAFLSPASQK

> Human Vγ J Region, TRFJP
[SEQ ID NO: 15]

GQELGKKIKVFGPGTKLIIT

> Human Vγ J Region, TRFJP1
[SEQ ID NO: 16]

GQELGKKIKVFGPGTKLIIT

> Human Vγ J Region, TRFJP2
[SEQ ID NO: 17]

SSDWIKTFAKGTRLIVTSP

> Human Vγ J Region, TRFJP1/2
[SEQ ID NO: 18]

NYYKKLFGSGTTLVVT

7. INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

8. EQUIVALENTS

While various specific embodiments have been illustrated and described, the above specification is not restrictive. It will be appreciated that various changes can be made without departing from the spirit and scope of the invention(s). Many variations will become apparent to those skilled in the art upon review of this specification.

What is claimed is:

1. A protein construct, comprising:
   a BTNL3/8 targeting moiety;
   a payload; and
   an optional linker linking the BTNL3/8 targeting moiety to the payload;
      wherein the BTNL3/8 targeting moiety comprises a T cell receptor (TCR) Vγ domain;
      wherein the TCR Vγ domain comprises a J region and complementarity-determining regions CDR1, CDR2, CDR3, and CDR4;
      wherein the TCR Vγ domain CDR4 is located between the CDR2 and the CDR3 regions of the TCR Vγ domain;
      wherein the amino acid at sequence position number 87 of the TCR Vγ domain is aspartic acid or histidine, and the amino acid at sequence position number 90 of the TCR Vγ domain is glycine or glutamic acid;
      wherein the remaining residues of the TCR Vγ domain CDR4 are, at each position, independently selected from the corresponding residues of a human or murine Vγ domain; and
      wherein the payload is a protein payload fused in-frame to the BTNL3/8 targeting moiety or is a small molecule.

2. The protein construct of claim 1, wherein the remaining residues of the TCR Vγ domain CDR4 are, at each residue position, independently selected from the corresponding residues of human Vγ4 domain, human Vγ2 domain, or mouse Vγ7 domain.

3. The protein construct of claim 1, wherein the amino acid sequence at position numbers 87-90 of the TCR Vγ domain comprises an amino acid sequence as set forth in SEQ ID NO: 1 or SEQ ID NO: 2.

4. The protein construct of claim 1, wherein the TCR Vγ domain comprises a human Vγ2 domain in which the amino acids of the CDR4 are substituted with aspartic acid or histidine at amino acid sequence position number 87 and substituted with glycine or glutamic acid at amino acid sequence position number 90, or wherein the TCR Vγ domain comprises a human Vγ4 domain.

5. The protein construct of claim 1, wherein the TCR Vγ domain CDR3 comprises a human or mouse Vγ CDR3.

6. The protein construct of claim 1, wherein the BTNL3/8 targeting moiety further comprises a paired TCR Vδ domain.

7. The protein construct of claim 6, wherein the BTNL3/8 targeting moiety comprises an amino acid sequence as set forth in SEQ ID NO: 9, SEQ ID NO: 10, or SEQ ID NO: 11.

8. The protein construct of claim 6, wherein the BTNL3/8 targeting moiety comprises a single chain in-frame fusion of the TCR Vγ domain and the TCR Vδ domain.

9. The protein construct of claim 6, wherein the TCR Vδ domain comprises a human Vδ domain selected from Vδ1, Vδ2, or Vδ5.

10. The protein construct of claim 1, further comprising:
    a first T cell receptor constant region,
    wherein the first T cell receptor constant region is fused in-frame to the C terminus of the TCR Vγ domain.

11. The protein construct of claim 10, wherein the first T cell receptor constant region is a human T cell receptor β constant region, a human T cell receptor α constant region, or a human T cell receptor γ constant region.

12. The protein construct of claim 6, further comprising:
    a first T cell receptor constant region,
    wherein the first T cell receptor constant region is fused in-frame to the C terminus of the TCR Vγ domain; and
    a second T cell receptor constant region,
    wherein the second T cell receptor constant region is fused in-frame to the C terminus of the paired TCR Vδ domain.

13. The protein construct of claim 12, wherein the second T cell receptor constant region is a human T cell receptor α constant region, a human T cell receptor β constant region, or a human T cell receptor δ constant region.

14. A recombinant γδ TCR protein, comprising:
    at least one sequence having at least 90% sequence identity to a sequence selected from the group consisting of SEQ ID NO: 9, SEQ ID NO: 10, and SEQ ID NO: 11,
    wherein the recombinant γδ TCR protein is capable of targeting BTNL3/8 expressing cells.

15. The protein construct of claim 1,
    wherein the optional linker comprises a peptide fused in-frame to the BTNL3/8 targeting moiety or is a molecule conjugated to the BTNL3/8 targeting moiety.

* * * * *